United States Patent
Igarashi

(10) Patent No.: US 8,723,940 B2
(45) Date of Patent: May 13, 2014

(54) ENDOSCOPE APPARATUS

(71) Applicant: Olympus Medical Systems Corp., Tokyo (JP)

(72) Inventor: Makoto Igarashi, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/910,394

(22) Filed: Jun. 5, 2013

(65) Prior Publication Data
US 2013/0329027 A1    Dec. 12, 2013

Related U.S. Application Data

(63) Continuation of application No. PCT/JP2012/078742, filed on Nov. 6, 2012.

(30) Foreign Application Priority Data

Mar. 30, 2012    (JP) .................................. 2012-082285

(51) Int. Cl.
*A61B 1/04* (2006.01)
*A61B 1/06* (2006.01)
*A61B 1/00* (2006.01)

(52) U.S. Cl.
CPC ... *A61B 1/06* (2013.01); *A61B 1/00* (2013.01); *A61B 1/04* (2013.01)
USPC ............................................................. 348/68

(58) Field of Classification Search
CPC ........ A61B 1/06; A61B 1/00; A61B 1/00009; A61B 1/00096; A61B 1/00188; A61B 1/05; A61B 1/0646; A61B 5/0084; A61B 1/00101; A61B 1/00165; A61B 1/04; A61B 1/0638; A61B 5/0075; G02B 23/24; H04N 2005/2255; H04N 5/02

USPC ............ 348/E07.085, E5.028, E5.029, E9.01, 348/65, 68, 70, 71; 600/103, 108, 109, 118, 600/160, 167, 476, 478

See application file for complete search history.

(56) References Cited

U.S. PATENT DOCUMENTS

| | | |
|---|---|---|
| 5,078,150 A | 1/1992 | Hara et al. |
| 2006/0241349 A1 | 10/2006 | Gono |
| 2007/0149854 A1 | 6/2007 | Igarashi |
| 2011/0228064 A1 * | 9/2011 | Sasaki .............................. 348/65 |

FOREIGN PATENT DOCUMENTS

| | | |
|---|---|---|
| EP | 1 576 920 A1 | 9/2005 |
| JP | 02-104332 A | 4/1990 |
| JP | 04-200433 A | 7/1992 |

(Continued)

*Primary Examiner* — Sath V Perungavoor
*Assistant Examiner* — Dakshesh Parikh
(74) *Attorney, Agent, or Firm* — Scully, Scott, Murphy & Presser, P.C.

(57) ABSTRACT

An endoscope apparatus includes: a light source device radiating at least one or more illumination lights having a predetermined wavelength band to a subject, and an image pickup device picking up an image of a return light from the subject. A band decomposition processing section of a video processor performs processing for decomposition into multiple spatial frequency bands, for a first image signal having a peak wavelength of spectral characteristic, between a wavelength band including a maximum value and a wavelength band at a minimum value with regard to an absorption characteristic of living tissue after image pickup by the image pickup device. An emphasis processing section of the video processor performs emphasis processing on the basis of a band image signal with a lowest spatial frequency among multiple band image signals obtained by the decomposition processing to generate an emphasis-corrected image signal.

16 Claims, 17 Drawing Sheets

(56) References Cited

FOREIGN PATENT DOCUMENTS

| | | |
|---|---|---|
| JP | 2004-202217 A | 7/2004 |
| JP | 2006-141711 A | 6/2006 |
| JP | 2008-023041 A | 2/2008 |
| JP | 2011-193983 A | 10/2011 |
| WO | WO 2004/052187 A1 | 6/2004 |

* cited by examiner

ENDOSCOPE APPARATUS

CROSS REFERENCE TO RELATED APPLICATION

This application is a continuation application of PCT/JP2012/078742 filed on Nov. 6, 2012 and claims benefit of Japanese Application No. 2012-082285 filed in Japan on Mar. 30, 2012, the entire contents of which are incorporated herein by this reference.

BACKGROUND OF THE INVENTION

1. Field of the Invention

The present invention relates to an endoscope apparatus, and in particular to an endoscope apparatus capable of displaying a blood vessel inside a subject.

2. Description of the Related Art

Conventionally, various kinds of minimally invasive examinations and operations using an endoscope have been performed in a medical field. A surgeon can insert an endoscope into a body cavity, observe a subject which has been image-picked up by an image pickup apparatus provided at a distal end portion of an endoscope insertion section, and treats a lesioned part using a treatment instrument inserted in a treatment instrument channel as necessary. An operation using an endoscope is advantageous in that a bodily burden on a patient is not heavy because an abdominal operation is not performed.

An endoscope apparatus is configured including an endoscope, an image processing apparatus connected to the endoscope and an observation monitor. An image of a legion is picked up by an image pickup device provided at a distal end portion of an endoscope insertion section, and the image is displayed on the monitor. The surgeon can make a diagnosis or perform necessary treatment, looking at the image displayed on the monitor.

Some endoscope apparatuses are capable of not only performing normal light observation using a white color light but also performing special light observation using a special light such as an infrared light in order to observe an internal blood vessel.

In the case of an infrared endoscope apparatus, for example, indocyanine green (ICG) having an absorption peak characteristic in a near infrared light near a wavelength of 805 nm is injected into a patient's blood as medicine. Then, infrared lights near wavelengths of 805 nm and 930 nm are radiated to the subject from a light source device in a time division manner. A signal of a subject image picked up by a CCD is inputted to a processor of the infrared endoscope apparatus. As for such an infrared endoscope apparatus, an apparatus is proposed in which the processor allocates an image near the wavelength of 805 nm to a green signal (G) and allocates an image near the wavelength of 930 nm to a blue signal (B), and outputs the images to a monitor as disclosed in, for example, Japanese Patent Application Laid-Open Publication No. 2000-41942. Since the image of the infrared light near the image of 805 nm which is well-absorbed by the ICG is allocated to green, the surgeon can observe an infrared image during administration of ICG with high contrast.

SUMMARY OF THE INVENTION

According to an aspect of the present invention, it is possible to provide an endoscope apparatus including: an illumination section radiating at least one or more illumination lights having a predetermined wavelength band to a subject; an image pickup section picking up an image of a return light from the subject based on radiation of the illumination section; a band decomposition processing section performing processing for decomposition into multiple spatial frequency bands, for a signal corresponding to a first wavelength band having a narrowband spectral characteristic, in a red band in a visible range between a wavelength band including a maximum value and a wavelength band including a minimum value with regard to a hemoglobin absorption characteristic of living tissue of the subject, after image pickup by the image pickup section; an emphasis processing section generating a signal obtained by performing emphasis correction for luminance adjustment for a band image signal with a lowest spatial frequency among multiple band image signals obtained by the decomposition processing by the band decomposition processing section; a color conversion processing section performing processing for giving a predetermined coefficient to the signal emphasis-corrected in the emphasis processing section and a signal corresponding to a second wavelength band having an absorption coefficient of the hemoglobin absorption characteristic lower than an absorption coefficient of the hemoglobin absorption characteristic of the signal corresponding to the first wavelength band and having such a spectral characteristic that a scattering characteristic of the living tissue is suppressed, and allocating the signals to respective color channels of BGR; and a display section displaying the signals allocated by the color conversion processing section.

According to an aspect of the present invention, it is possible to provide an endoscope apparatus including: an illumination section radiating at least one or more illumination lights having a predetermined wavelength band to a subject; an image pickup section picking up an image of a return light from the subject based on radiation of the illumination section; a band decomposition processing section performing processing for decomposition into multiple spatial frequency bands, for a signal corresponding to a first wavelength band having a narrowband spectral characteristic and a signal corresponding to a second wavelength band having an absorption coefficient of the hemoglobin absorption characteristic lower than an absorption coefficient of the hemoglobin absorption characteristic of the signal corresponding to the first wavelength band and having such a narrowband spectral characteristic that a scattering characteristic of living tissue is suppressed, between a wavelength band including the maximum value and a wavelength band at the minimum value with regard to an absorption characteristic of the living tissue, after image pickup by the image pickup device; a spectral estimation section generating a spectral estimation image signal by spectral estimation processing of a band image signal with a low spatial frequency among multiple band image signals generated by the band decomposition processing section for each of the signal corresponding to the first wavelength band and the signal corresponding to the second wavelength band; and an emphasis processing section performing emphasis processing for the spectral estimation image signal obtained by the spectral estimation processing of the spectral estimation section.

DETAILED DESCRIPTION OF THE PREFERRED EMBODIMENTS

Embodiments of the present invention will be described below with reference to drawings.

First Embodiment

Configuration of Endoscope Apparatus

An embodiment of the present invention will be described below with reference to drawings.

Figure 1:
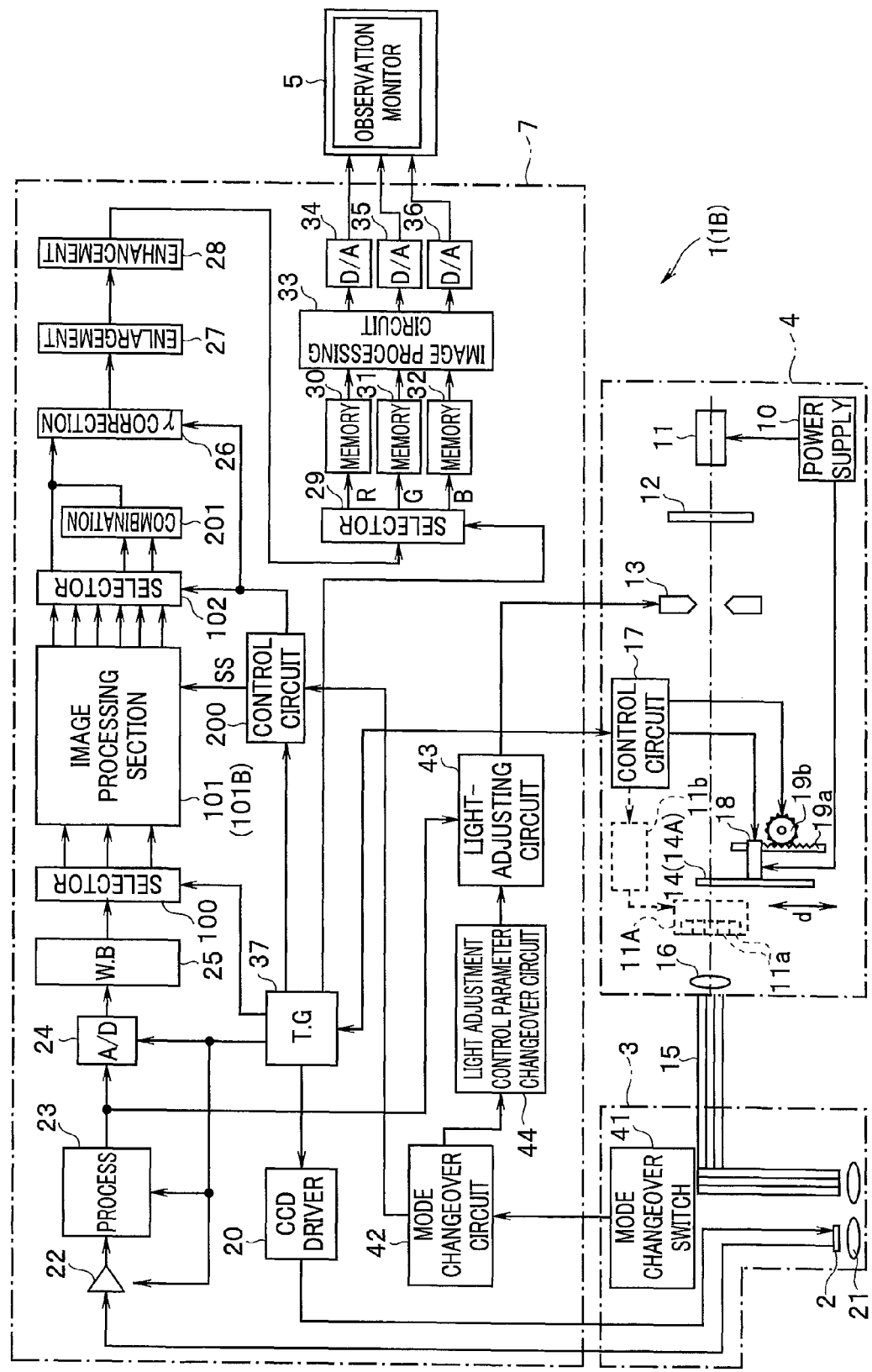
FIG. 1 is a configuration diagram showing a configuration of an endoscope apparatus according to a first embodiment of the present invention.

First, a configuration of an endoscope apparatus according to the present embodiment will be described. FIG. 1 is a configuration diagram showing the configuration of the endoscope apparatus according to the present embodiment.

As shown in FIG. 1, an endoscope apparatus 1 of the present embodiment is configured with an electronic endoscope 3 having a CCD 2, which is an image pickup device, as biological image information acquiring means or a living body image information acquiring section to be inserted into a body cavity to pick up an image of intra-body cavity tissue, a light source device 4 which supplies an illumination light to the electronic endoscope 3, and a video processor 7 which performs signal processing of an image pickup signal from the CCD 2 of the electronic endoscope 3 and displays an endoscopic image on an observation monitor 5. The endoscope apparatus 1 has two modes of a normal light observation mode and a narrowband light observation mode. Note that, in the description below, since the normal light observation mode of the endoscope apparatus 1 is the same as a conventional normal light observation mode, description of a configuration of the normal light observation mode is omitted, and the narrowband light observation mode will be mainly described.

The CCD 2 constitutes an image pickup section or image pickup means for receiving a return light of an illumination light radiated to a subject to pick up an image of the subject.

The light source device 4 as illumination means or an illumination section is configured being provided with a xenon lamp 11 which emits an illumination light (white color light), a heat ray cut filter 12 which cuts off a heat ray of the white color light, a diaphragm device 13 which controls a light amount of the white color light via the heat ray cut filter 12, a rotating filter 14 as band limiting means or a band limiting section which causes the illumination light to be frame-sequential lights, a condensing lens 16 which collects the frame-sequential lights via the rotating filter 14 on an incident face of a light guide 15 arranged in the electronic endoscope 3, and a control circuit 17 which controls rotation of the rotating filter 14. The xenon lamp 11, the rotating filter 14 and the light guide 15 constitute an irradiating section or irradiating means that illuminates the subject with the illumination light.

Figure 2:
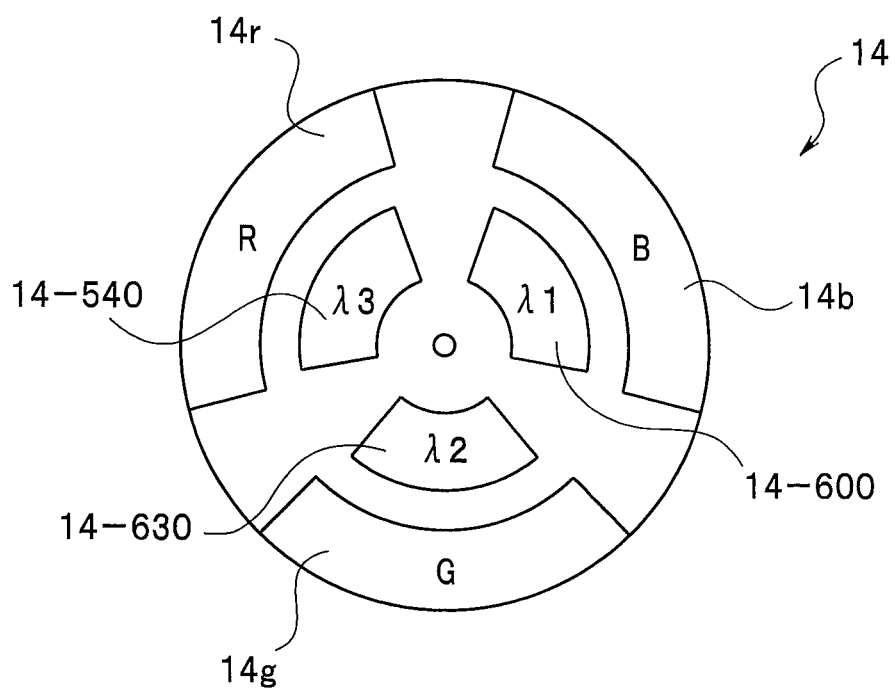
FIG. 2 is a diagram showing a configuration of a rotating filter 14 according to the first embodiment.

FIG. 2 is a diagram showing a configuration of the rotating filter 14. The rotating filter 14 is a filter which transmits a light from the xenon lamp 11 which is a light source. The rotating filter 14 as a wavelength band limiting section or wavelength band limiting means is configured in a disc shape as shown in FIG. 2 and with a structure having a rotating shaft at the center. The rotating filter 14 has two filter groups. On an outer circumferential side of the rotating filter 14, an R (red) filter section 14r, a G (green) filter section 14g and a B (blue) filter section 14b constituting a filter set for outputting frame-sequential lights having a spectral characteristic for normal light observation are arranged along a circumferential direction as a first filter group.

On an inner circumferential side of the rotating 14, three filters 14-600, 14-630 and 14-540 that transmit lights having three predetermined narrowband wavelengths are arranged along the circumferential direction as a second filter group.

The filter 14-600 is configured to transmit a light near a wavelength of 600 nm ($\lambda$1) as a narrowband light. The filter 14-630 is configured to transmit a light near a wavelength of 630 nm ($\lambda$2) as a narrowband light. The filter 14-540 is configured to transmit a light near a wavelength of 540 nm ($\lambda$1) as a narrowband light.

In the case of near the wavelength of 600 nm, "near" means that the light is a narrowband light having a center wavelength of 600 nm and having a distribution in a range of a width of, for example, 20 nm with the wavelength of 600 nm as the center (i.e., from a wavelength of 590 nm before the wavelength of 600 nm to a wavelength of 610 nm after the wavelength of 600 nm). The same goes for the other wavelengths, the wavelength of 630 nm and the wavelength of 540 nm to be described later.

The rotating filter 14 is arranged on an optical path extending from the xenon lamp 11, which is a section of emitting an illumination light, to an image pickup surface of the CCD 2. The rotating filter 14 limits at least one (here, three) wavelength band among multiple wavelength bands of the illumination light to be narrowed in each mode.

The control circuit 17 controls a motor 18 for causing the rotating filter 14 to rotate to control the rotation of the rotating filter 14.

A rack 19a is connected to the motor 18. A motor not shown is connected to a pinion 19b. The rack 19a is attached to be screwed with the pinion 19b. The control circuit 17 can move the rotating filter 14 in a direction indicated by an arrow d by controlling rotation of the motor connected to the pinion 19b. Therefore, the control circuit 17 controls the motor connected to the pinion 19b so that, according to a mode switching operation by the user to be described later, the first filter group is positioned on the optical path in the normal light observation mode, and the second filter group in the narrowband light observation mode.

Note that, electric power is supplied from a power supply section 10 to the xenon lamp 11, the diaphragm device 13, the rotating filter motor 18, and the motor (not shown) connected to the pinion 19b.

Thus, the light source device 4 constitutes illumination means or an illumination section that radiates at least one or more illumination lights (here, three narrowband lights) having a predetermined wavelength band to a subject in the narrowband light observation mode. Here, two of the three illumination lights are narrowband lights for emphasizingly displaying a blood vessel in a deep part 1 to 2 mm from an epithelium, and the remaining one is a narrowband light as a third illumination light which can be transmitted over a predetermined distance from an epithelium of a subject, here, within a range near the epithelium.

The video processor 7 includes a CCD driving circuit 20 which is a CCD driver, an amplifier 22, a process circuit 23, an A/D converter 24, a white balance circuit (hereinafter referred to as W. B) 25, a selector 100, an image processing section 101, a selector 102, a γ correction circuit 26, an enlargement circuit 27, an emphasis circuit 28, a selector 29, synchronizing memories 30, 31 and 32, an image processing circuit 33, D/A converters 34, 35 and 36, a timing generator (hereinafter referred to as T. G) 37, a mode changeover circuit 42, a light-adjusting circuit 43, a light adjustment control parameter changeover circuit 44, a control circuit 200, and a combination circuit 201 as display image generating means or a display image generating section.

The CCD driving circuit 20 drives the CCD 2 provided in the electronic endoscope 3 and causes the CCD 2 to output frame-sequential image pickup signals synchronized with rotation of the rotating filter 14. The amplifier 22 amplifies the frame-sequential image pickup signals obtained by picking up an image of intra-body cavity tissue by the CCD 2 via an objective optical system 21 provided at a distal end of the electronic endoscope 3.

The process circuit 23 performs correlated double sampling, noise removal and the like for the frame-sequential image pickup signals via the amplifier 22. The A/D converter 24 converts the frame-sequential image pickup signals having passed through the process circuit 23 to digital frame-sequential image signals.

The W. B 25 performs gain adjustment and executes white balance processing for the frame-sequential image signals digitized by the A/D converter 24 so that, for example, brightness of an R signal of the image signal and brightness of a B signal of the image signal are equal with each other with reference to a G signal of the image signal.

Note that white balance adjustment at the W. B 25 is performed with reference to luminance of a return light of a narrowband light near the wavelength of 600 nm.

The selector 100 distributes and outputs frame-sequential image signals from the W. B 25 to respective sections in the image processing section 101.

The image processing section 101 is an image signal processing section or image signal processing means that converts an RGB image signal for normal light observation or three image signals for narrowband light observation from the selector 100 to an image signal for display. The image processing section 101 outputs, according to a selection signal SS from the control circuit 200 based on a mode signal, image signals in the normal light observation mode and in the narrowband light observation mode to the selector 102.

The selector 102 sequentially outputs frame-sequential image signals of the image signal for normal light observation and the image signal for narrowband light observation from the image processing section 101 to the γ correction circuit 26 and the combination circuit 201.

The γ correction circuit 26 applies γ correction processing to the frame-sequential image signals from the selector 102 or the combination circuit 201. The enlargement circuit 27 performs enlargement processing of the frame-sequential image signals which have been γ-correction-processed by the γ correction circuit 26. The emphasis circuit 28 applies edge emphasis processing to the frame-sequential image signals which have been enlargement-processed by the enlargement circuit 27. The selector 29 and the synchronizing memories 30, 31 and 32 are for synchronizing the frame-sequential image signals from the emphasis circuit 28.

The image processing circuit 33 reads out respective frame-sequential image signals stored in the synchronizing memories 30, 31 and 32 and performs moving image color shift correction processing and the like. The D/A converters 34, 35 and 36 convert the image signals from the image processing circuit 33 into RGB analog video signals and output the RGB analog video signals to the observation monitor 5. The T. G 37 inputs a synchronization signal synchronized with the rotation of the rotating filter 14, from the control circuit 17 of the light source device 4, and outputs various timing signals to the respective circuits in the video processor 7 described above.

In the electronic endoscope 2, a mode changeover switch 41 for switching between the normal light observation mode and the narrowband light observation mode is provided. An output of this mode changeover switch 41 is outputted to the mode changeover circuit 42 in the video processor 7. The mode changeover circuit 42 of the video processor 7 outputs a control signal to a light adjustment control parameter changeover circuit 44 and the control circuit 200. The light-adjusting circuit 43 controls the diaphragm device 13 of the light source device 4 on the basis of light adjustment control parameters from the light adjustment control parameter changeover circuit 44 and an image pickup signal which has passed through the process circuit 23 to perform proper brightness control.

Each circuit in the video processor 7 executes predetermined processing corresponding to a specified mode. Processing corresponding to each of the normal light observation mode and the narrowband light observation mode is executed, and an image for normal light observation or an image for narrowband light observation is displayed on the observation monitor 5. The observation monitor 5 is display means or a display section that displays an emphasis-corrected image signal.

(Whole Process Flow of Narrowband Light Observation)

Next, an overall rough flow of the narrowband light observation in the present embodiment will be briefly described below.

Figure 3:
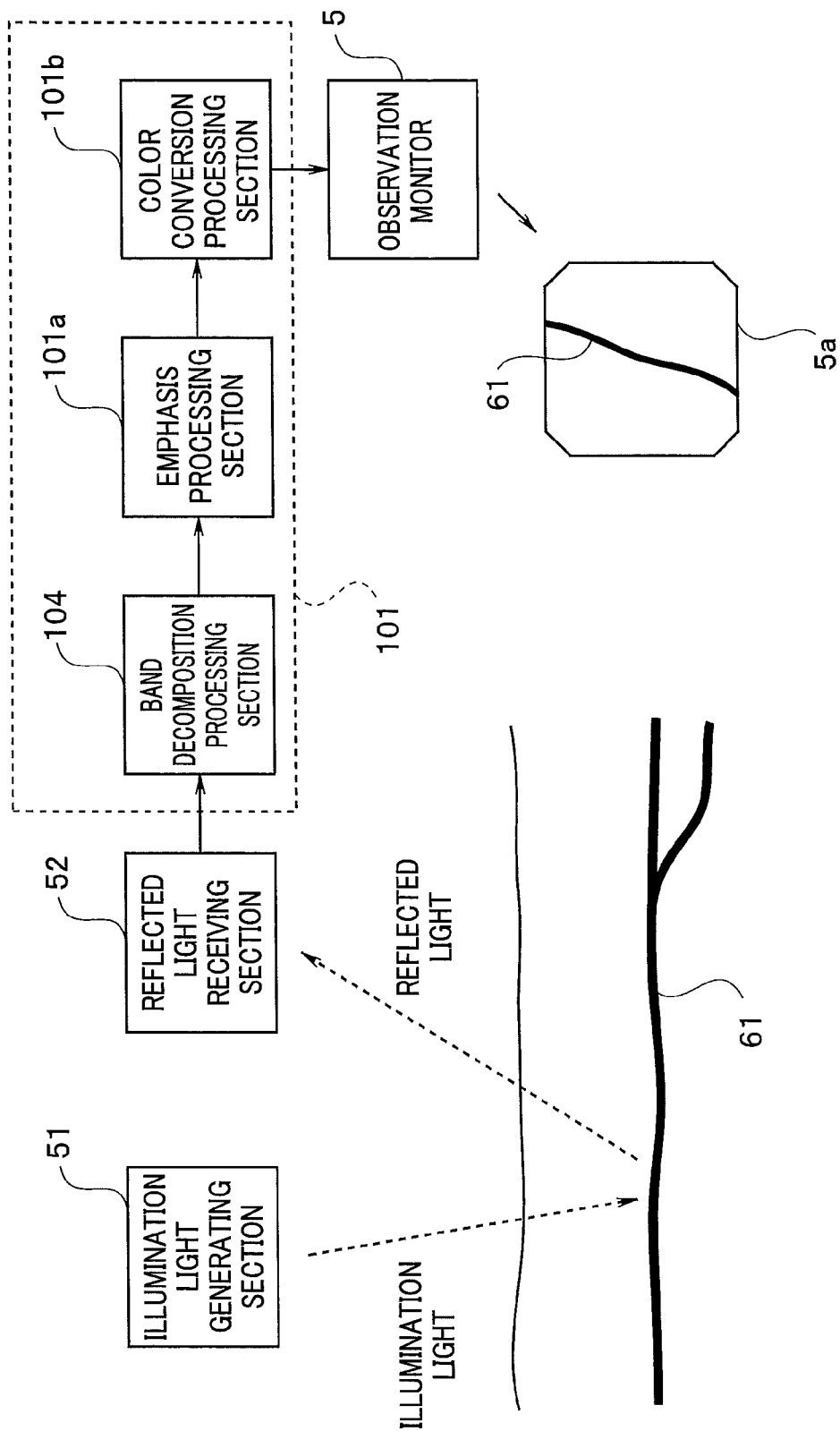
FIG. 3 is a diagram for illustrating a whole process flow in narrowband light observation according to the first embodiment.

FIG. 3 is a diagram for illustrating a whole process flow in the narrowband light observation according to the present embodiment.

A surgeon inserts the insertion section of the endoscope into a body cavity and positions the distal end portion of the insertion section of the endoscope near a lesioned part under the normal light observation mode. When confirming the treatment target lesioned part, the surgeon operates the mode changeover switch 41 to switch the endoscope apparatus 1 to the narrowband light observation mode in order to observe a relatively thick blood vessel in a deep part having a diameter of, for example, 1 to 2 mm, and running from a submucosa to a muscularis propria.

Under the narrowband light observation mode, the control circuit 17 of the endoscope apparatus 1 controls the motor connected to the pinion 19$b$ to move the position of the rotating filter 14 so that a light transmitted through the second filter group is emitted from the light source device 4. Furthermore, the control circuit 200 also controls the various circuits in the video processor 7 to perform image processing for observation by a narrowband wavelength.

As shown in FIG. 3, in the narrowband light observation mode, an illumination light having a narrowband wavelength is emitted from the distal end portion of the insertion section of the endoscope 3, from an illumination light generating section 51, transmitted through a stratum mucosum, and radiated to a blood vessel 61 running in a submucosa and a muscularis propria. Here, the illumination light generating section 51 is configured including the light source device 4, the rotating filter 14, the light guide 15, and the like, and emits an illumination light from the distal end of the endoscope insertion section. By rotation of the rotating filter 14, a narrowband light near the wavelength of 600 nm, a narrowband light near the wavelength of 630 nm and a narrowband light near the wavelength of 540 nm are successively and sequentially emitted from the light source device 4 and radiated to a subject.

Each of reflected lights of the narrowband light near the wavelength of 600 nm, the narrowband light near the wavelength of 630 nm and the narrowband light near the wavelength of 540 nm is received by a reflected light receiving section 52 which is the CCD 2. The CCD 2 outputs image pickup signals of the respective reflected lights, and supplied to the selector 100 via the amplifier 22 and the like. The selector 100 holds a first image signal P1 near the wavelength of 600 nm, a second image signal P2 near the wavelength of 630 nm and a third image signal P3 near the wavelength of 540 nm and supplies the image signals to the image processing section 101 according to a predetermined timing from the T. G 37. The image processing section 101 includes a band decomposition processing section 104, an emphasis processing section 101$a$ and a color conversion processing section 101$b$ for the narrowband light observation mode.

For example, in ESD in which, for example, a stratum mucosum of an inner wall of a digestive tract such as a stomach, a gullet and a large bowel, where a lesioned part exists, is dissected and ablated with the use of the endoscope apparatus 1, the surgeon has to be careful not to cut a relatively thick blood vessel in tissue with an electric surgical knife or the like. When setting the endoscope apparatus 1 to the narrowband light observation mode, the surgeon can clearly depict blood vessels under the surface of living tissue.

(Band Decomposition Processing of Image Processing Section)

The band decomposition processing section 104 of the image processing section 101 in FIG. 1 performs spatial frequency division processing for at least one wavelength image by spatial frequency division processing.

Figure 4:
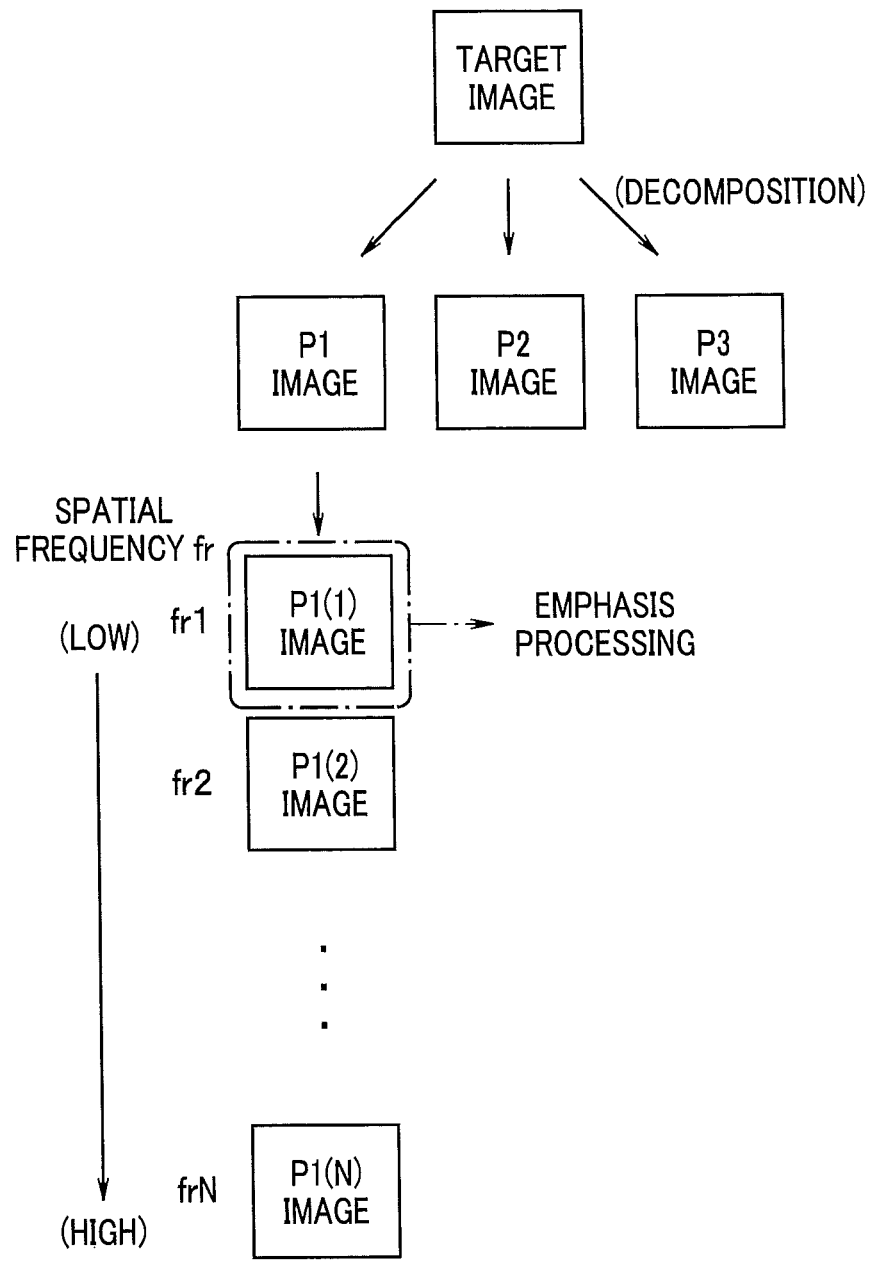
FIG. 4 is a diagram for illustrating a process for generating images of multiple frequency bands from one wavelength image and performing emphasis processing for one of the generated images of multiple frequency bands, according to the first embodiment.

FIG. 4 is a diagram for illustrating a process for generating images of multiple frequency bands from one wavelength image and performing emphasis processing for one of the generated images of multiple frequency bands.

Figure 5:
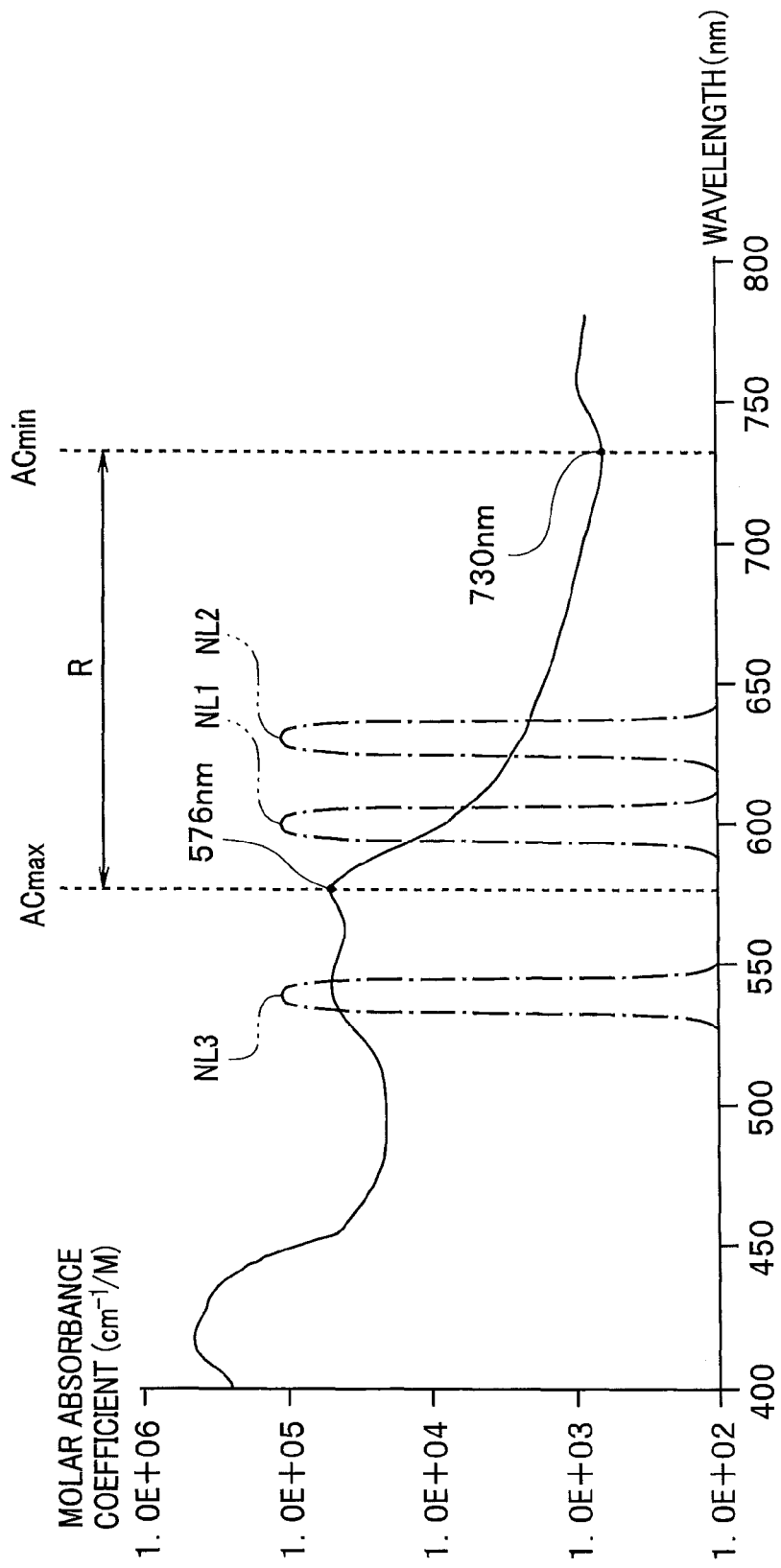
FIG. 5 is a diagram showing a light absorption characteristic of venous blood according to the first embodiment.

As shown in FIG. 4, the band decomposition processing section 104 divides a first image signal P1 near the wavelength of 600 nm into image signals of N (N: a natural number of 1 or more) spatial frequency bands (hereinafter referred to as band image signals) by spatial frequency analysis, for example, by spatial frequency division processing. As shown in FIG. 5 (to be described later), the first image signal P1 is an image signal having a peak wavelength of spectral characteristic between a wavelength band including a maximum value ACmax and a wavelength band at a minimum value ACmin of an absorption characteristic of living tissue after image pickup by the image pickup device 2.

That is, the band decomposition processing section 104 constitutes band decomposition processing means or a band decomposition processing section for performing processing for decomposition into multiple spatial frequency bands, for the image signal P1 having the peak wavelength of spectral characteristic, between the wavelength band including the maximum value ACmax and the wavelength band at the minimum value ACmin of the absorption characteristic of living tissue, after image pickup by the image pickup device 2.

Note that the band decomposition processing section 104 may also be able to divide a second image signal P2 near the wavelength of 630 nm into N band image signals. That is, the band decomposition processing section 104 may generate, for each of m (m: a natural number of 1 or more) wavelength images, N band images, N being equal to or more than 2. In FIG. 4, m is 1, and N band image signals P1(1), P1(2), ..., P1(N) are generated from the first image signal P1.

In that case, the band decomposition processing section 104 also performs the processing for decomposition into multiple spatial frequency bands, for the second image signal P2 having the peak wavelength of spectral characteristic, between the wavelength band including the maximum value ACmax and the wavelength band at the minimum value ACmin of the absorption characteristic of living tissue after image pickup by the image pickup device 2. The emphasis processing section 101$a$ performs emphasis processing on the basis of a predetermined band image signal (for example, a band image signal with a lowest spatial frequency) among multiple band image signals obtained by the decomposition processing for the second image signal P2 in addition to the band image signals related to the first image signal P1 to generate an emphasis-corrected image signal.

Thus, the band decomposition processing section 104 constitutes band decomposition processing means or a band decomposition processing section, or spatial frequency division processing means or a spatial frequency division processing section that performs the processing for decomposition into multiple spatial frequency bands, for an image of at least one wavelength band of a medical image, to generate multiple band images.

Here, the N spatial frequency bands are spatial frequencies fr1, fr2, ..., frN. The spatial frequency fr1 is the lowest, and the spatial frequency is gradually higher from fr2 toward frN. Therefore, among the N band image signals P1(1), P1(2), ..., P1(N), the band image signal P1(1) is an image signal with the lowest spatial frequency. For example, a band image signal near P1(1) has information about a living structure such as a thicker blood vessel in a deep part. On the other hand, among the N band image signals P1(1), P1(2), ..., P1(N), the band image signal P1(N) is an image signal with the highest spatial frequency. For example, a band image signal near P1(N) has information about an uneven surface structure such as a thinner blood vessel or a gland structure in a mucosal epithelium. Note that each band image signal is generated, for example, by performing spatial frequency filtering processing using a mask corresponding to each spatial frequency frk, for a wavelength image signal.

The emphasis processing section 101a performs image processing to be described later for image emphasis of the blood vessel 61, and the color conversion processing section 101b allocates each image signal to each channel of RGB of the observation monitor 5 and supplies the image signal to the selector 102. As a result, the relatively thick blood vessel 61 in a deep mucosa is displayed with high contrast on a screen 5a of the observation monitor 5. Thereby, the surgeon can apply the ESD to the lesioned part while paying attention to the blood vessel 61 running in the submucosa and the muscularis propria, which is displayed on the observation monitor 5.

Here, a light absorption characteristic of venous blood will be described. FIG. 5 is a diagram showing the light absorption characteristic of venous blood. A vertical axis in FIG. 5 indicates a molar absorbance coefficient (cm−1/M) and a horizontal axis indicates wavelength. Note that, though illumination lights of the three narrowband lights are influenced by a scattering characteristic of living tissue itself, the scattering characteristic of the living tissue itself decreases almost monotonously relative to increase in wavelength, and, therefore, FIG. 5 will be described as a diagram of the light absorption characteristic of the living tissue.

In general, venous blood includes oxyhemoglobin ($HbO_2$) and reduced hemoglobin (Hb) (hereinafter, generically referred to simply as hemoglobin) at the rate of about 60:40 to 80:20. Light is absorbed by hemoglobin, but the absorption coefficient differs according to light wavelength. FIG. 5 shows the light absorption characteristic for each wavelength from 400 nm to about 800 nm, and, within a range from 550 nm to 750 nm, the absorption coefficient shows a maximum value at a point of a wavelength of about 576 nm, and a minimum value at a point of a wavelength of about 730 nm.

In the narrowband light observation mode, three narrowband lights are radiated, and each return light is received by the CCD 2.

A narrowband light near the wavelength of 600 nm (hereinafter referred to as a first narrowband light NL1) is a light of a wavelength band within a wavelength band R from a maximum value ACmax (here, an absorption coefficient at the wavelength of 576 nm) to a minimum value ACmin (here, an absorption coefficient at the wavelength of 730 nm) of the absorption characteristic of hemoglobin.

A narrowband light near the wavelength of 630 nm (hereinafter referred to as a second narrowband light NL2) is also a light within the wavelength band R from the maximum value ACmax to the minimum value ACmin of the absorption characteristic of hemoglobin. However, it is a light of a wavelength band longer than the wavelength of the first narrowband light NL1 with a lower absorption coefficient in which the scattering characteristic of living tissue is suppressed. That the scattering characteristic is suppressed means that the scattering coefficient decreases toward the long wavelength side.

That is, the light source device 4 radiates the first illumination light NL1 having the peak wavelength of spectral characteristic and the second illumination light NL2 having a value lower than the image signal P1 by the first illumination light NL1 with regard to the absorption characteristic and having a peak wavelength of such a spectral characteristic that the scattering characteristic of the living tissue is suppressed, between the wavelength band including the maximum value ACmax and the wavelength band at the minimum value ACmin of the absorption characteristic of living tissue.

A narrowband light near the wavelength of 540 nm (hereinafter referred to as a third narrowband light NL3) is a light of a wavelength band outside the wavelength band R from the maximum value ACmax to minimum value ACmin of the absorption characteristic of hemoglobin, which is an illumination light which can be transmitted by a predetermined distance from an epithelium of a mucosal surface of a subject.

The CCD 2 outputs an image pickup signal of each of images of the three narrowband lights. Therefore, each image includes multiple pixel signals based on each of return lights of the first, second and third narrowband lights NL1, NL2 and NL3.

Figure 6:
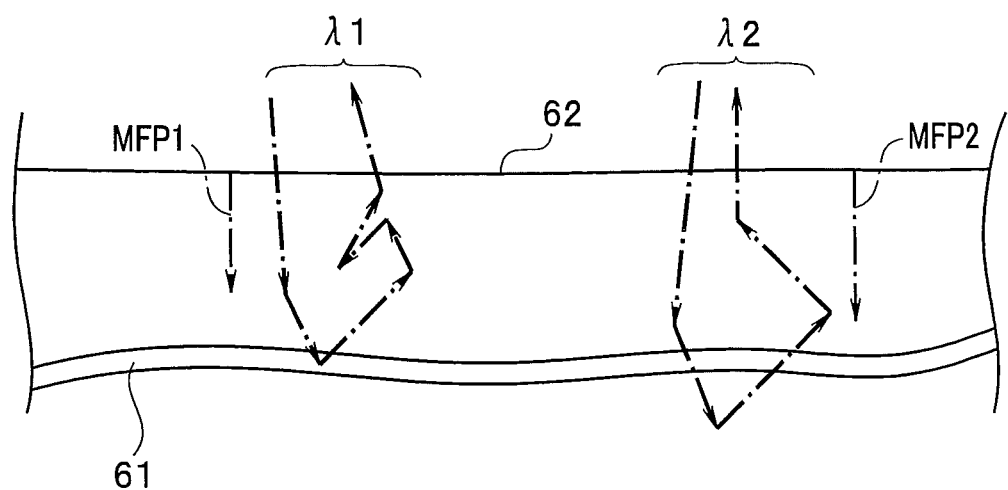
FIG. 6 is a diagram for illustrating light propagation volume in living tissue, of a first narrowband light NL1 ($\lambda$1) and a second narrowband light NL2 ($\lambda$2) according to the first embodiment.

Furthermore, light propagation in living tissue of the first and second narrowband lights NL1 and NL2 which are illumination lights will be described. FIG. 6 is a diagram for illustrating light propagation volume in living tissue of the first narrowband light NL1 ($\lambda 1$) and the second narrowband light NL2 ($\lambda 2$). Each of the first and second narrowband lights NL1 and NL2 repeats multiple scattering processes in living tissue, and, as a result, emitted from a mucosal surface as return lights. The first and second narrowband light NL1 and NL2 have mean free paths MFP1 and MFP2, respectively. The mean free path MFP1 of the first narrowband light NL1 is shorter than the mean free path MFP2 of the second narrowband light NL2.

As shown in FIG. 6, the first narrowband light NL1 with the wavelength of 600 nm ($\lambda 1$) reaches the vicinity of the blood vessel 61, and the second narrowband light NL2 with the wavelength of 630 nm ($\lambda 2$) reaches a position slightly deeper than the blood vessel 61.

Note that a mean free path of the third narrowband light NL3 near the wavelength of 540 nm is shorter than the mean free paths MFP1 and MFP2 of the two narrowband lights NL1 and NL2, and the third narrowband light NL3 reaches only up to a relatively shallow area of an epithelium of a mucosal surface, though it is not shown in FIG. 6.

Figure 17:
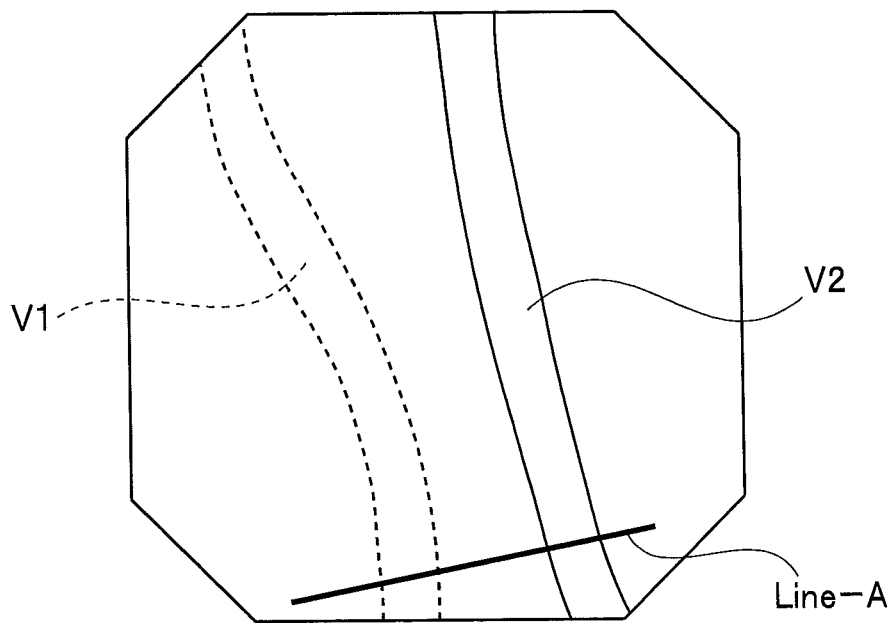
FIG. 17 is a schematic diagram of an image obtained by photographing an inside of an abdominal cavity of an animal using a spectral endoscope apparatus capable of radiating a narrowband illumination light chronologically at intervals of 10 nm of center wavelength.

FIG. 17 is a schematic diagram of an image obtained by photographing an inside of an abdominal cavity of an animal using a spectral endoscope apparatus capable of radiating a narrowband illumination light chronologically at intervals of 10 nm of center wavelength. More specifically, FIG. 17 shows an image in which monochrome images of 540 nm, 600 nm and 630 nm are allocated to a B channel, a G channel and an R channel, respectively. A blood vessel V1 and a blood vessel V2 in the image are thick blood vessels running from an upper left direction to a lower right direction in the image. The blood vessel V1 is positioned deeper from a mucosal surface than the blood vessel V2. Here, monochrome images of a total of fifteen patterns have been photographed at 10 nm-step intervals from 540 nm over to 680 nm.

Figure 18:
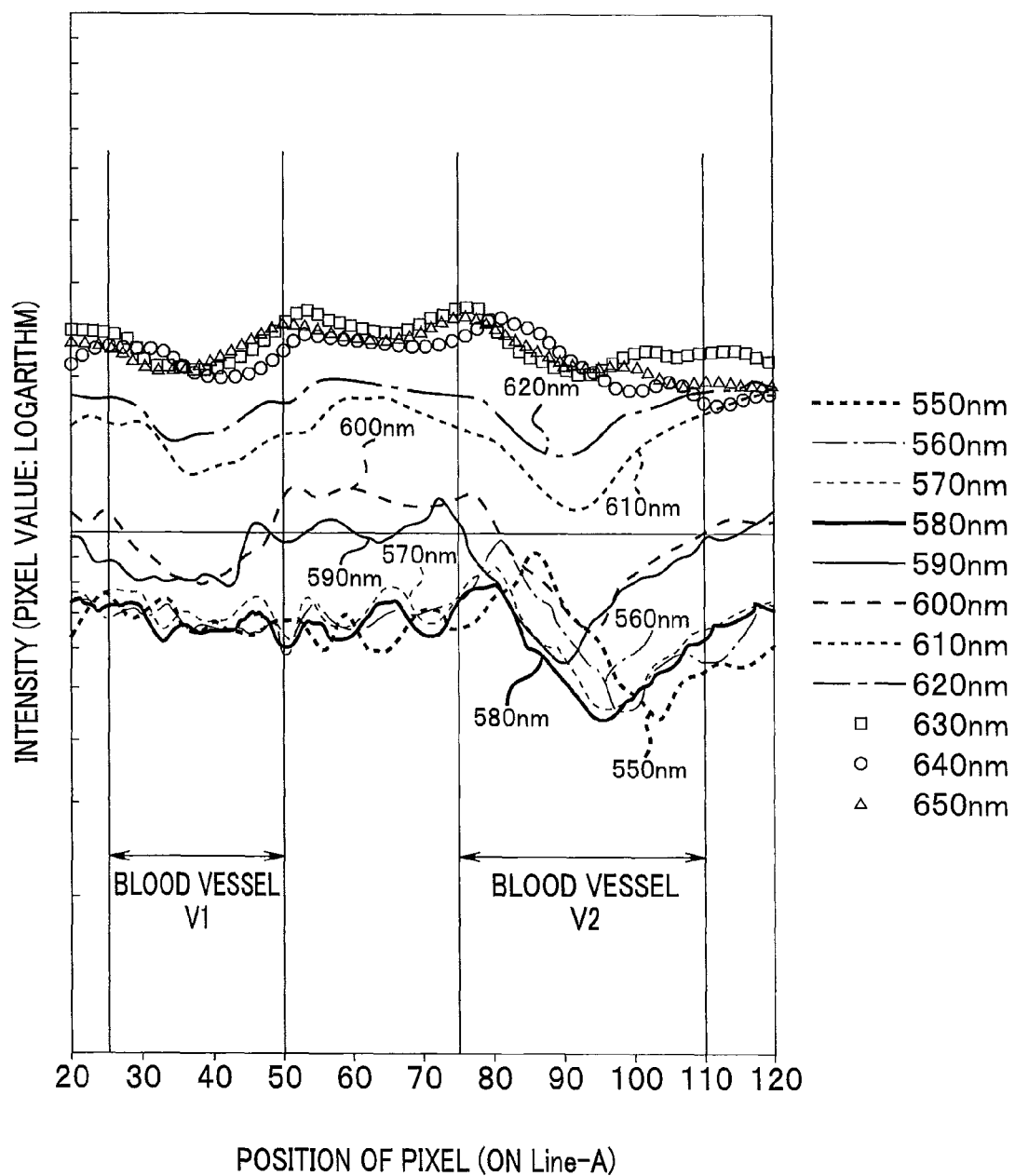
FIG. 18 is a graph showing, for multiple monochrome images shown in FIG. 17, intensities (logarithmically displayed pixel values) on Line-A in each image are shown on a vertical axis.

FIG. 18 is a graph showing, for the multiple monochrome images shown in FIG. 17, intensities (logarithmically displayed pixel values) on Line-A in each image are shown on a vertical axis. A horizontal axis in FIG. 18 indicates positions of pixels on Line-A in each image. Positions of pixels of the blood vessel V1 are near 25 to 50, and positions of pixels of the blood vessel V2 are near 75 to 110. It is seen from FIG. 18 that an illumination wavelength the intensity of which decreases in both of the blood vessel V2 existing in a relatively shallow part and the blood vessel V1 positioned in a deep part, that is, a wavelength in which an illumination light is strongly absorbed in the blood vessels V1 and V2 is about 590 to 620 nm.

Therefore, in order to detect a blood vessel existing from a relatively shallow part to a deep part, an about 590 to 620 nm narrowband light is important wavelength information. The blood vessel V1 exists in a part about 1 to 2 mm deep from a mucosal surface. Note that a result of this experiment almost corresponds to a result of the theoretical calculation by the Beer-Lambert law described before (a relatively thick blood vessel can be displayed with high contrast by using a narrowband light within a range from 15 nm before and 15 nm after the wavelength of 600 nm).

As described above, the illumination means or the illumination section that includes the light source device 4 radiates the narrowband light NL1 which is an illumination light having the peak wavelength of spectral characteristic and the illumination light NL2 which is an illumination light having a value lower than the narrowband light NL1 with regard to a return light absorption characteristic and having a peak wavelength of such a spectral characteristic that the scattering characteristic of the living tissue is suppressed, between the wavelength band including the maximum value ACmax and the wavelength band at the minimum value ACmin of the absorption characteristic of living tissue.

Furthermore, the illumination means or the illumination section that includes the light source device 4 also radiates the third illumination light NL3 which can be transmitted over a predetermined distance from an epithelium of a subject.

(Emphasis Processing of Image Processing Section)

Next, processing in the image processing section 101 will be described. In the normal light observation mode, a blood vessel in a deep part 1 to 2 mm from an epithelium of a subject in a picked-up endoscopic image is not displayed or is difficult to be displayed on the endoscopic image on the observation monitor 5.

In comparison, in the narrowband light observation mode, when a deep-part blood vessel exists in a picked-up endoscopic image, the blood vessel is displayed on the endoscopic image.

An image of the narrowband light NL1 with the wavelength of 600 nm ($\lambda$1) is configured by multiple lines, and each line includes multiple pixels. The emphasis processing section 101$a$ performs emphasis processing by multiplying a pixel value of each pixel of a band image signal P1(1) with a lowest spatial frequency among multiple band images obtained by performing band decomposition processing for an image signal of the narrowband light NL1 with the wavelength of 600 nm ($\lambda$1) by a predetermined gain coefficient, and outputs an emphasis-corrected image signal BEP1 ($\lambda$1) which has been emphasis-corrected, to the color conversion section 101$b$.

That is, the emphasis processing section 101$a$ constitutes image processing means or an image processing section that performs emphasis processing on the basis of a predetermined band image signal among multiple band image signals obtained by decomposition processing by the band decomposition processing section 104 to generate an emphasis-corrected image signal. Here, the emphasis processing section 101$a$ generates the emphasis-corrected image signal BEP1 ($\lambda$1) obtained by emphasis correction by performing processing for emphasizing only a band image signal with a lowest spatial frequency among multiple band image signals obtained by band decomposition processing.

Note that, though the emphasis processing section 101$a$ emphasizes only the band image signal with the lowest spatial frequency among the multiple band image signals obtained by band decomposition processing here, emphasis processing may be performed for a band image signal other than the band image signal with the lowest spatial frequency (for example, a band image signal P1(2) with a second lowest spatial frequency may be emphasized). Note that emphasis processing may be performed for two or more band image signals with a low spatial frequency among the multiple spatial frequency bands.

(Color Conversion Processing of Image Processing Section)

Next, processing in the color conversion processing section 101$b$ will be described. A second image signal P2 ($\lambda$2), a third image signal P3 ($\lambda$3) and the emphasis-corrected image signal BEP1 ($\lambda$1) are inputted to the color conversion processing section 101$b$.

In the color conversion processing section 101$b$, processing for allocating the second image signal P2 ($\lambda$2), the third image signal P3 ($\lambda$3) and the emphasis-corrected image signal BEP1 ($\lambda$1) to RGB channels is performed.

Here, for example, by a following expression (1), a brightness value 1 mA ($\lambda$1) of the emphasis-corrected image signal BEP1 ($\lambda$1), a brightness value Im ($\lambda$2) of the second image signal P2 ($\lambda$2) and a brightness value Im ($\lambda$3) of the third image signal P3 ($\lambda$3) are allocated to the RGB channels.

$$\begin{pmatrix} B \\ G \\ R \end{pmatrix} = \begin{pmatrix} 1 & 0 & 0 \\ 0 & 1 & 0 \\ 0 & 0 & 1 \end{pmatrix} \begin{pmatrix} Im(\lambda 3) \\ ImA(\lambda 1) \\ Im(\lambda 2) \end{pmatrix} \quad \text{Equation (1)}$$

According to the equation (1), the relatively thick blood vessel 61 in a deep part is displayed in rather reddish color and is easily identified by the surgeon.

Since the narrowband light near the wavelength of 540 nm is used as the third narrowband light NL3, a capillary vessel and bleeding existing in a relatively shallow area from the surface of living tissue are displayed in almost yellow.

In the color conversion processing 101$b$, a following equation (2) may be used instead of the above equation (1).

$$\begin{pmatrix} B \\ G \\ R \end{pmatrix} = \begin{pmatrix} 1 & 0 & 0 \\ 1 & 0 & 0 \\ 0 & 1 & 0 \end{pmatrix} \begin{pmatrix} Im(\lambda 3) \\ ImA(\lambda 1) \\ Im(\lambda 2) \end{pmatrix} \quad \text{Equation (2)}$$

According to the equation (2), since the blood vessel 61 in a deep part is displayed in blue or bluish green as well as the capillary vessels in an epithelium being displayed from red to brown, the vessels can be easily identified by the surgeon.

Furthermore, note that a following equation (3) may be used instead of the above equation (1) in the color conversion processing 101$b$.

$$\begin{pmatrix} B \\ G \\ R \end{pmatrix} = \begin{pmatrix} 1 & 0 & 0 \\ 0.5 & 0.5 & 0 \\ 0 & 1 & 0 \end{pmatrix} \begin{pmatrix} Im(\lambda 3) \\ ImA(\lambda 1) \\ Im(\lambda 2) \end{pmatrix} \quad \text{Equation (3)}$$

Furthermore, note that a following equation (4) may be used instead of the above equation (1) in the color conversion processing 101b. Here, α takes a numerical value nearly from 1.0 to 1.5, β takes a numerical value nearly from 2.0 to 2.6, and γ takes a numerical value nearly from 2.5 to 3.3 (for example, α:β:γ=0.56:1.00:1.17). In this case, color tone of a blood vessel in a deep part is blush green, and color tone of a mucosa is similar to that of normal observation, the surgeon can perform observation without stress. By setting α, β and γ to numerical values nearly from 2.3 to 2.7, nearly from 2.3 to 2.7, and nearly from 1.7 to 2.1, respectively (for example, α:β:γ=1.00:1.00:0.76), it becomes easy to observe blood vessels in an epithelium and a deep part.

$$\begin{pmatrix} B \\ G \\ R \end{pmatrix} = \begin{pmatrix} \alpha & 0 & 0 \\ \beta & 0 & 0 \\ 0 & \gamma & 0 \end{pmatrix} \begin{pmatrix} Im(\lambda 3) \\ ImA(\lambda 1) \\ Im(\lambda 2) \end{pmatrix} \quad \text{Equation (4)}$$

Note that another example of the channel allocation by the color conversion processing section 101b will be described. For example, at the time of giving treatment, the narrowband light near the wavelength of 540 nm may be allocated to the B channel, the narrowband light near the wavelength of 630 nm to the G channel, and the narrowband light near the wavelength of 600 nm (that is, the emphasis-corrected image signal BEP1 (λ1)) to the R channel, instead of the above equation (1).

At the time of giving a diagnosis, the narrowband light near the wavelength of 540 nm can be allocated to the B channel and the G channel, and the narrowband light near the wavelength of 600 nm or the narrowband light near the wavelength of 630 nm can be allocated to the R channel.

Here, color balance adjustment will be described.

For example, in the case of allocating the narrowband light near the wavelength of 540 nm, the narrowband light near the wavelength of 630 nm and the narrowband light near the wavelength of 600 nm to the B channel, the G channel and the R channel, respectively, like an equation (1), it is desirable to amplify the signal of the B channel relative to the signal of the R channel. The signal intensity of the narrowband light near the wavelength of 600 nm is not corrected, and the two signals of the signal of the narrowband light near a wavelength of 540 nm allocated to the B channel and the signal of the narrowband light near the wavelength of 630 nm are adjusted so that the intensity of the former signal is 0.7 to 2.5 times as high as the intensity of the latter signal. Note that the color conversion processing may be performed after performing the color balance adjustment, or the color balance processing may be performed after the color conversion processing.

Thereby, color tone difference among a mucosa, fibrous tissue in a white color tone, bleeding in yellow, a carbonized area in black, and a thick blood vessel in color tones from red to magenta becomes more remarkable, and it is possible to obtain a display image from which the surgeon can give treatment or diagnosis more easily.

A color balance adjustment circuit for such color balance adjustment may be provided for a previous stage of the W. B 25 in FIG. 1. In that case, when intensities of illumination lights of the narrowband light near the wavelength of 540 nm and the narrowband light near the wavelength of 630 nm are almost equal to each other, the color balance adjustment circuit sets the signal of the narrowband light near the wavelength of 540 nm allocated to the B channel to be about 0.7 to 1.5 times, and the signal of the narrowband light near the wavelength of 630 nm to be about 0.6 to 1.0 times.

Note that the color balance adjustment may be performed by the color conversion processing section 101b, or may be performed by the light source device 4 adjusting the intensities of the illumination lights, or may be performed by adjusting transmittance of each color of the color filters of the image pickup device.

(Whole Process Flow in Image Processing Section)

Figure 7:
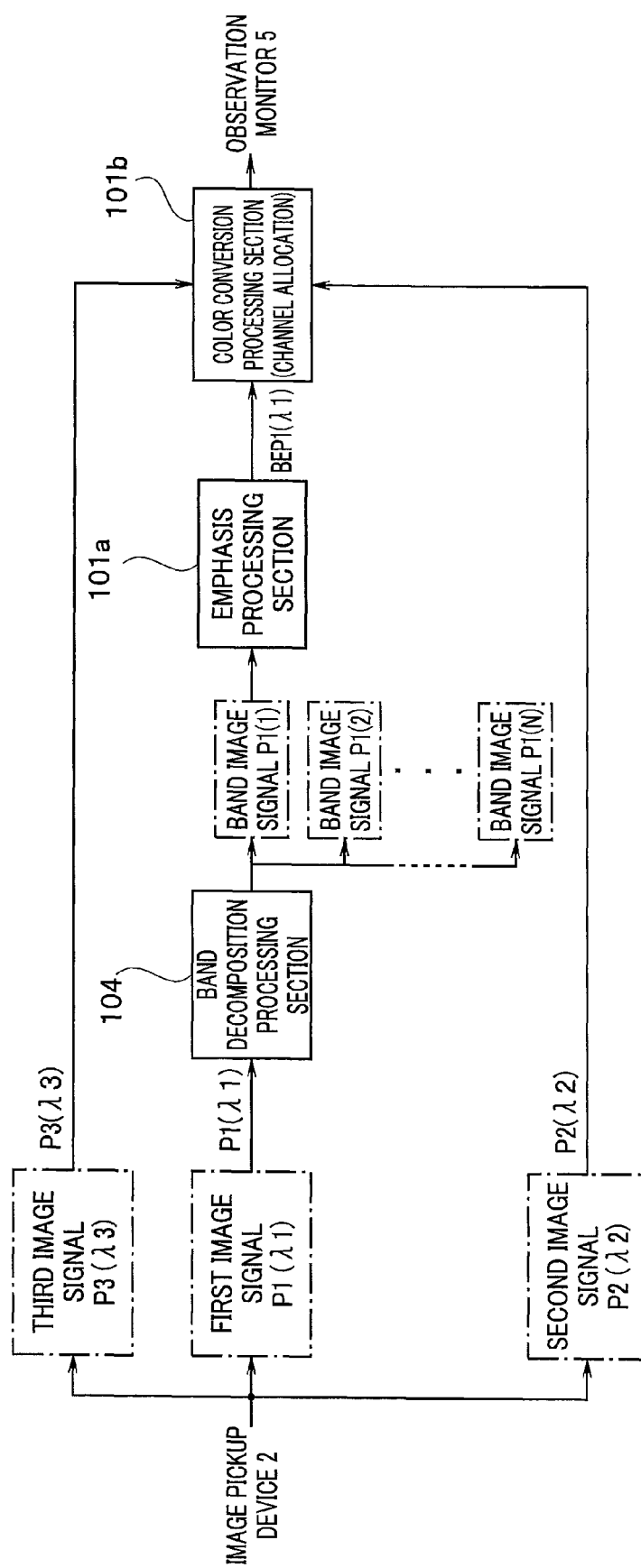
FIG. 7 is a diagram for illustrating a flow of processing for an image obtained from an image pickup device 2 in an image processing section 101 according to the first embodiment.

Next, a flow of processing for an image obtained from the image pickup device 2 in the image processing section 101 will be described. FIG. 7 is a diagram for illustrating the flow of the processing for an image obtained from the image pickup device 2 in the image processing section 101.

As shown in FIG. 7, three images from the image pickup device 2 are inputted to the image processing section 101 as first to third image signals P1, P2 and P3. For the image signal P1 among the inputted three images, band decomposition processing by the band decomposition processing section 104 is performed. The band decomposition processing section 104 decomposes the image signal P1 into predetermined multiple spatial frequencies, here, N bands fr1 to frN to generate N band image signals P1(1), P1(2), . . . , P1(N).

Emphasis processing is performed for the band image signal P1(1) with a lowest spatial frequency among N band image signals, for example, by multiplication by a predetermined gain coefficient by the emphasis processing section 101a. That is, luminance is adjusted so that only the band image signal P1(1), which is an image signal with the lowest spatial frequency, is emphasized. Thus, only the band image signal P1(1) in which only an image of a relatively thick blood vessel is included is emphasized.

The color conversion processing section 101b performs the color conversion processing by allocation of channels as described above for the second image signal P2, the third image signal P3 and the emphasis-corrected image signal BEP1 (λ1) and outputs the signals to the observation monitor 5.

As described above, narrowband lights having an absorption characteristic as described above between a maximum value and minimum value of the absorption characteristic of living tissue, as shown in FIG. 5 are radiated to a living mucosa, and, band decomposition processing for band decomposition into multiple band image signals is performed for images of obtained return lights. Then, by performing emphasis processing for at least one band image signal with a low spatial frequency among the obtained multiple band image signals, a relatively thick blood vessel existing in a relatively deep part of the living mucosa is emphasized and displayed on a screen of the observation monitor 5. Therefore, the surgeon can perform desired treatment such as ESD, looking at and confirming the relatively thick blood vessel.

Note that, though band decomposition processing by spatial frequency division processing is performed for the first image signal P1 near the wavelength of 600 nm, and emphasis processing is performed for a band image signal with a lowest spatial frequency among band image signals in the example described above, spatial frequency division processing may be performed for the second image signal P2 near the wavelength of 630 nm, and emphasis processing may be performed for a band image signal with a lowest spatial frequency among band image signals depending on a place of living tissue or a state of a treated part (for example, a place or state in which a surface of the living tissue is covered with blood).

In that case, when the narrowband light near the wavelength of 540 nm is allocated to the B channel, the narrowband light near the wavelength of 600 nm to the G channel, and the narrowband light near the wavelength of 630 nm (that is, the emphasis-corrected image signal BEP2 ($\lambda$2)) to the R channel, a thick blood vessel is displayed in blue or bluish green.

Furthermore, note that, though band decomposition processing is performed for one image signal in the example described above, it is also possible to perform the band decomposition processing for, for example, both of the first image signal P1 near the wavelength of 600 nm and the second image signal P2 near the wavelength of 630 nm, select a band image with a low spatial frequency (for example, with a lowest spatial frequency) from the two respective band decomposition processes, and perform emphasis processing for both of the band images to be emphasis-corrected image signals.

In this case, when the narrowband light near the wavelength of 540 nm is allocated to the B channel, the narrowband light near the wavelength of 600 nm (that is, the emphasis-corrected image signal BEP1 ($\lambda$1)) to the G channel, and the narrowband light near the wavelength of 630 nm to the R channel, a thick blood vessel is displayed in bluish color.

Though emphasis processing is performed for a band image signal with a lowest spatial frequency in the example described above, the emphasis processing may be performed not for the band image signal with the lowest spatial frequency but for a band image signal with a second or third lowest spatial frequency.

Furthermore, in the endoscope apparatus 1 described above, a blood vessel existing near an epithelium of living mucosa can be displayed with the use of the third narrowband light NL3.

For example, since the third narrowband light NL3 near the wavelength of 540 nm is used, a state of capillary vessels in an epithelium is also displayed on the screen of the observation monitor 5 together with a thick blood vessel. Thus, the surgeon can use an endoscopic image on the screen of the observation monitor 5 not only for treatment but also for diagnosis of living tissue, for example, diagnosis of existence of cancer or range diagnosis for identifying a range of cancer, and for discrimination diagnosis for judging whether an affected part is benignant or malignant, from a state of capillary vessels, for example, degree of concentration or dispersion of the capillary vessels. Furthermore, it is possible to perform invasive depth diagnosis and the like taking into account of a blood vessel in a deeper part.

Note that, though the light source device 4 described above generates an illumination light of a desired wavelength band using the xenon lamp 11, the rotating filter 14 and the like, in the endoscope apparatus 1, as indicated by dotted lines, the light source device 4 may be configured to include a light emitting section 11A including a light emitting diode group 11a including multiple light emitting diodes (LEDs) that emit desired wavelength, for example, each of wavelengths of RGB corresponding to the first filter group and each of wavelengths near 600 nm and near 630 nm corresponding to the second filter group. In that case, the light emitting section 11A and the light guide 15 constitute an irradiating section that irradiates a subject with illumination light.

For example, in FIG. 1, instead of the xenon lamp 11, the heat ray cut filter 12, the diaphragm device 13, the rotating filter 14 and the like, the light emitting section 11A indicated by a dotted line is provided in the light source device 4.

Furthermore, the light source device 4 is provided with a driving circuit 11b for driving each of the light emitting diodes of the light emitting section 11A at predetermined timings according to each mode. The light emitting section 11A having multiple LEDs 11a receives power source from the power supply 10 and is controlled and driven by the driving circuit 11b under a control signal from the control circuit 17.

When the endoscope apparatus 1 is configured with the use of such a light source device, the same advantages as described above can be also obtained.

Note that the light emitting section 11A may employ a laser diode (LD) that emits predetermined multiple narrowband lights.

In the case where the light source device is mounted with any of a heat light source, an LED and an LD, and the CCD 2 is not only a monochrome image pickup device but is provided with RGB color filters or complementary color filters as the wavelength band limiting means or the wavelength band limiting section, advantages equal to those described above can be obtained.

The second narrowband light NL2 shown in FIG. 5 may be a light of a longer wavelength band than the minimum value ACmin of the absorption characteristic of hemoglobin (here, an absorption coefficient at the wavelength of 730 nm). That is, as for the wavelength of the second narrowband light NL2, such a wavelength band that the absorption coefficient is lower than the wavelength of the first narrowband light NL1 and the scattering characteristic of living tissue is suppressed, for example, 740 nm, 770 nm, 805 nm, 810 nm, 850 nm, 870 nm, 880 nm, 910 nm, 940 nm, 1020 nm or 1300 nm can be used to obtain advantages equal to those described above (for example, when the narrowband light NL2 is set to any wavelength from 740 nm to 1300 nm, the narrowband light NL1 is set to any wavelength equal to or longer than 576 nm and at least equal to or shorter than 630 nm). Note that the second narrowband light NL2 can be also generated even when any of a xenon light source, an LED and an LD is mounted as a light source device.

As described above, according to the present embodiment described above, it is possible to provide an endoscope apparatus capable of clearly displaying a blood vessel in a deep mucosa without complicated work of medicine administration being performed.

Second Embodiment

In the first embodiment, at least one narrowband light is actually radiated as an illumination light to living tissue. The band decomposition processing described above is performed for an image of a return light thereof, and emphasis processing is performed for at least one band image signal obtained by the band decomposition processing. In the present embodiment, however, the at least one narrowband light is not actually radiated to living tissue. Image information of a return light of each narrowband light is obtained by so-called spectral estimation, and band decomposition processing as described above is performed for a spectral image signal obtained by the spectral estimation. Then, emphasis processing is performed for at least one band image signal obtained by the band decomposition processing. That is, though the at least one narrowband light is generated by an illumination device having a rotating filter or a light emitting device such as a light emitting diode, and the band decomposition processing is performed for images of return lights thereof in the first embodiment described above, image signals corresponding to three narrowband lights are obtained by spectral estimation processing, and band decomposition processing is performed for spectral estimation image signals obtained by the spectral estimation in the present embodiment.

Figure 8:
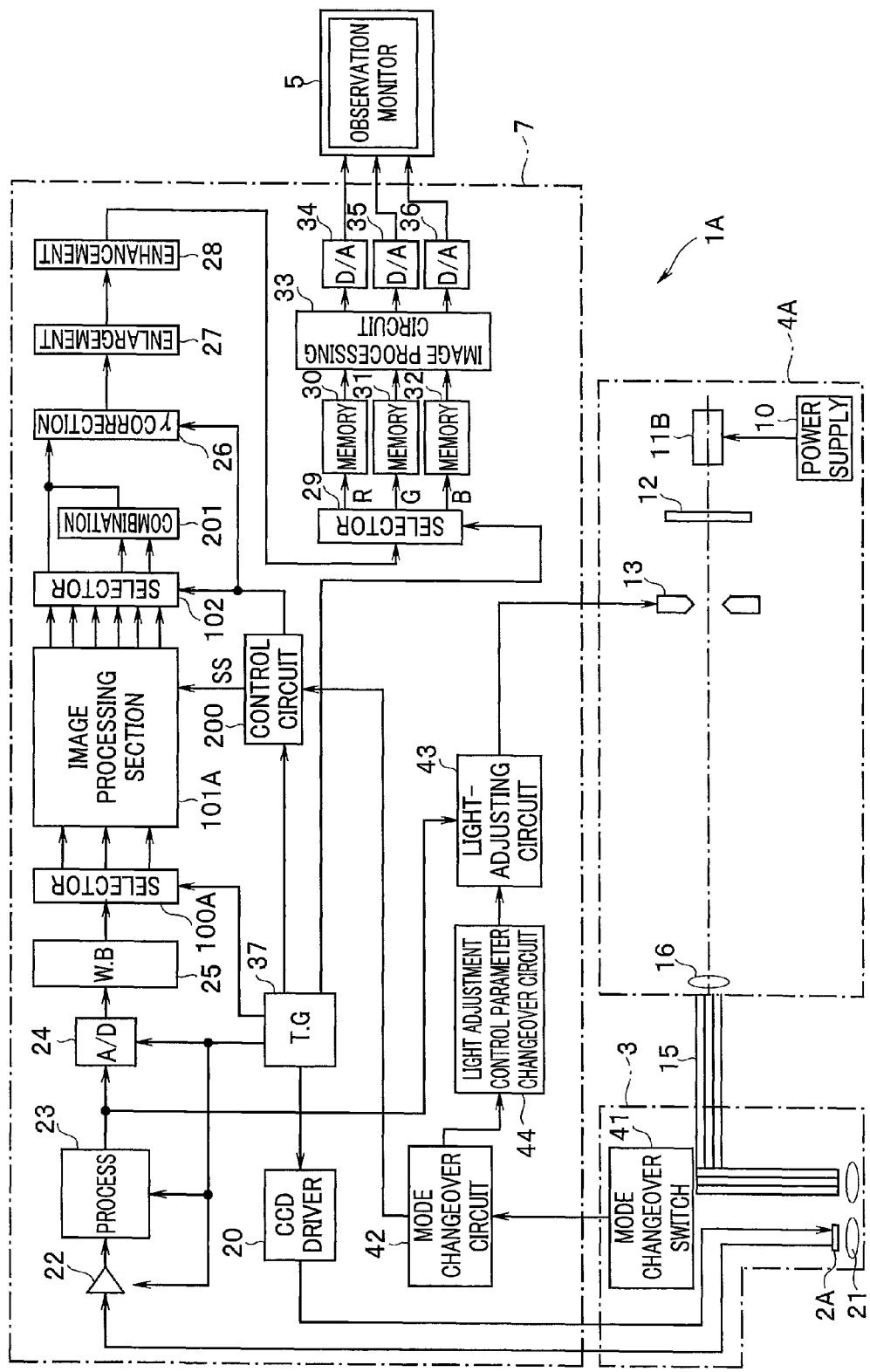
FIG. 8 is a configuration diagram showing a configuration of an endoscope apparatus 1A according to a second embodiment.

FIG. 8 is a configuration diagram showing a configuration of an endoscope apparatus 1A according to the second embodiment of the present invention. In FIG. 8, the same components as shown in FIG. 1 are denoted by the same reference numerals and signs and description thereof is omitted.

As shown in FIG. 8, a light source device 4A is configured, including a lamp 11B that emits a white light, the heat ray cut filter 12, and the diaphragm device 13. An illumination light from the light source device 4A is radiated to a subject via the light guide 15. Note that the lamp 11B may emit a light other than a white color light.

An image pickup device 2A provided at the distal end of the insertion section of the endoscope 3 is a color image pickup device. The image pickup device 2A is, for example, a color CCD and includes RGB color filters on an image pickup surface. A return light from the subject is received by each pixel section of the image pickup surface via the RGB color filters, which are wavelength band limiting means or wavelength band limiting sections, and image signals of three colors of RGB are outputted from the image pickup device 2A.

A selector 100A outputs the three image signals of RGB to an image processing section 101A. The image processing section 101A has a spectral estimation section, and, in the narrowband light observation mode, generates a spectral estimation image signal near the wavelength of 600 nm, a spectral estimation image signal near the wavelength of 630 nm and a spectral estimation image signal near the wavelength of 540 nm.

Figure 9:
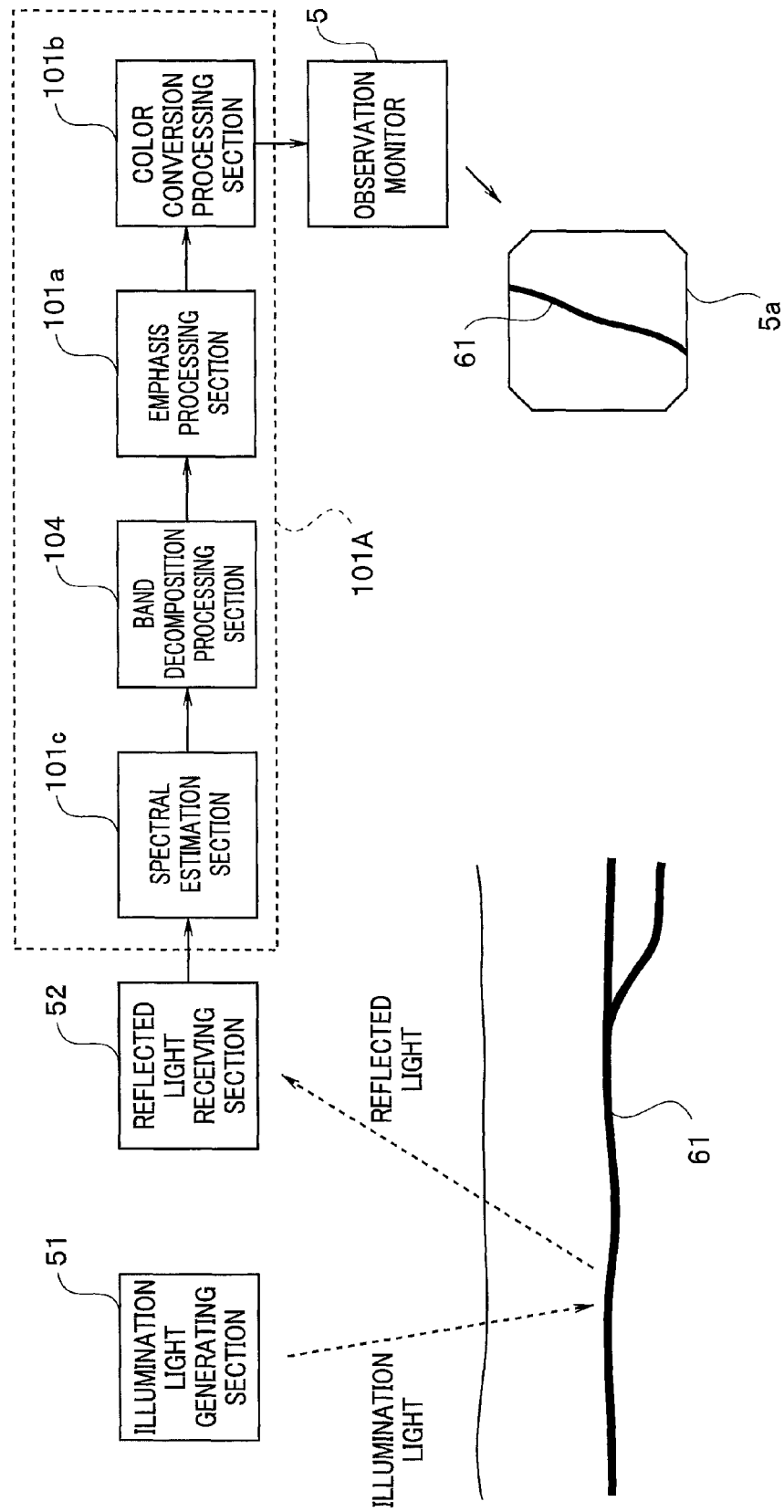
FIG. 9 is a diagram for illustrating a whole process flow in narrowband light observation according to the second embodiment.

FIG. 9 is a diagram for illustrating a whole process flow in the narrowband light observation according to the present embodiment. In FIG. 9, the same components as those in FIG. 3 are given the same reference numerals and signs, and description thereof is omitted. The image processing section 101A includes a spectral estimation section 101c in addition to the emphasis processing section 101a, the color conversion processing section 101b and the band decomposition processing section 104. The spectral estimation section 101c extracts a first spectral estimation image signal e1 near the wavelength of 600 nm, a second spectral estimation image signal e2 near the wavelength of 630 nm and a third spectral estimation image signal e3 near the wavelength of 540 nm from three images of RGB by spectral estimation processing and outputs the signals to the band decomposition processing section 104.

More specifically, the spectral estimation section 101c calculates n-dimensional spectral images from three inputs by matrix operations on the basis of a priori information given in advance, and selectively outputs e1, e2 and e3 among the calculated n-dimensional spectral estimation image signals. The spectral estimation section 101c is configured to calculate and output the spectral estimation image signal e1 near the wavelength of 600 nm, the spectral estimation image signal e2 near the wavelength of 630 nm and the spectral estimation image signal e3 near the wavelength of 540 nm using matrix operations and the like.

The first, second and third spectral estimation image signals outputted from the spectral estimation section 101c are band-decomposed in the band decomposition processing section 104. The processes of the band decomposition processing section 104, the emphasis processing section 101a and the color conversion processing section 101b at stages after the spectral estimation section 101c are the same as the processes described in the first embodiment described above.

Figure 10:
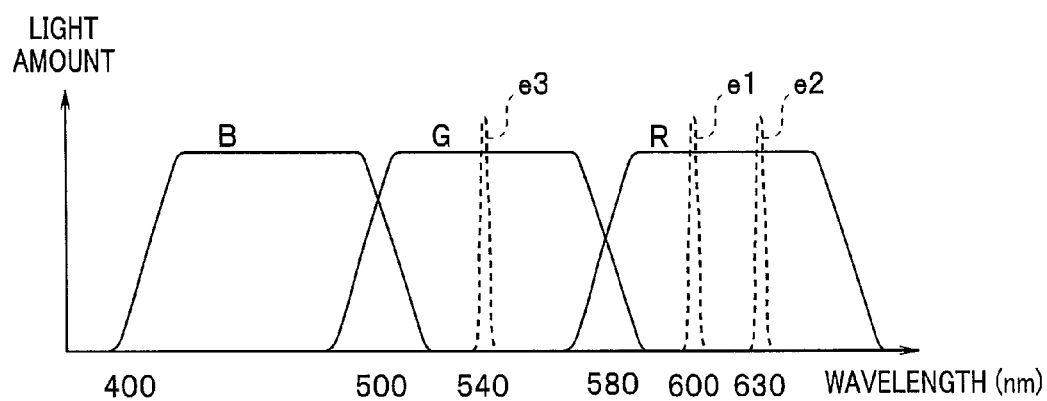
FIG. 10 is a diagram showing a spectral characteristic for illustrating a case of estimating three narrowband-light spectral image signals e1, e2 and e3 from three broadband-light image signals B, G and R according to the second embodiment.

FIG. 10 is a diagram showing a spectral characteristic for illustrating a case of estimating the three narrowband-light spectral image signals e1, e2 and e3 from three broadband-light image signals B, G and R. The three broadband lights B, G and R in FIG. 10 are obtained by the color filters of the image pickup device 2A, and image signals of the three broadband lights B, G and R are inputted to the spectral estimation section 101c.

The spectral estimation section 101c estimates the three narrowband-light spectral estimation image signals e1, e2 and e3 from the three broadband light image signals B, G and R by spectral estimation processing. The spectral estimation image signal e1 near the wavelength of 600 nm, the spectral estimation image signal e2 near the wavelength of 630 nm and the spectral estimation image signal e3 near the wavelength of 540 nm are obtained from the broadband-light image signals B, G and R having wavelength bands as shown in FIG. 10 by spectral estimation processing. Here, two narrowband-light spectral estimation image signals e1 and e2 within the wavelength band R between the maximum value ACmax and the minimum value ACmin in FIG. 5 and a spectral estimation image signal e3 outside the wavelength band R are obtained by spectral estimation, and the spectral estimation image signals e1, e2 and e3 are supplied to the band decomposition processing section 104.

Note that the three spectral image signals e1, e2 and e3 may be obtained from image signals of two broadband lights among the three broad lights, for example, image signals of the broadband lights G and R by spectral estimation processing.

Furthermore, note that the image signals of the three (or two) broadband lights may be obtained not with the use of the color filters of the color image pickup device but by applying return lights of three (or two) illumination lights generated by arranging a first filter group of a rotating filter having such a sensitivity characteristic that an image signal having a spectral characteristic as shown in FIG. 10 is obtained, on an optical path in the light source device, to a monochrome image pickup device.

As described above, the spectral estimation section 101c generates and outputs the three spectral estimation image signals e1, e2 and e3 by spectral estimation processing on the basis of at least two image pickup signals of return lights from a subject. Furthermore, the spectral estimation section 101c also generates and outputs the spectral estimation image signal e3 corresponding to a return light based on radiation of an illumination light which can be transmitted by a predetermined distance from an epithelium of a subject on the basis of the at least two image pickup signals. As described above, the processes in the band decomposition processing section 104, the emphasis processing section 101a and the color conversion processing section 101b are similar to those of the first embodiment.

Therefore, advantages similar to those of the endoscope apparatus 1 described above can be also obtained by the endoscope apparatus 1A of the present embodiment.

Next, a modification of spectral estimation will be described.

Though multiple narrowband-light spectral image signals are estimated from multiple broadband-light image signals in the spectral estimation processing described above, spectral estimation processing is not limited to such a method, and a method as described below is also possible.

A first method is for estimating three spectral image signals from image signals of two broadband lights and an image signal of one narrowband light. Since a narrowband-light image signal is used, accuracy of spectral estimation can be increased.

Figure 11:
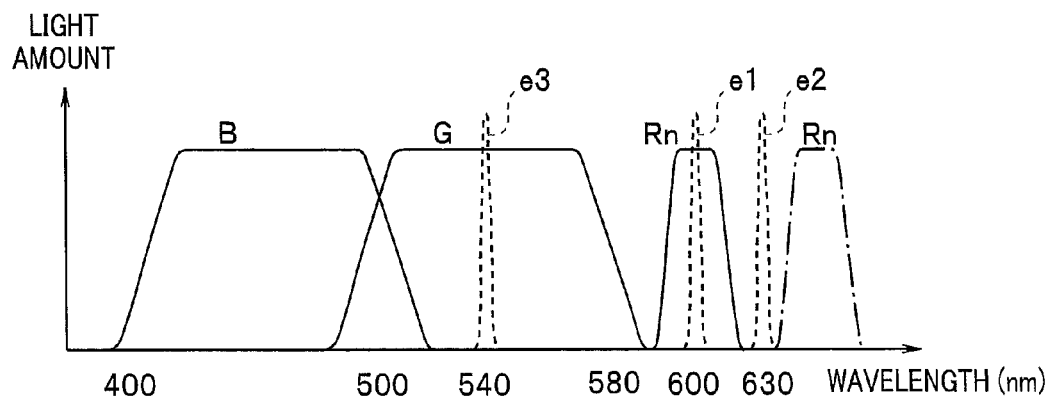
FIG. 11 is a diagram showing a spectral characteristic for illustrating a case of estimating three narrowband-light spectral image signals from two broadband-light image signals and one narrowband-light image signal, according to the second embodiment.

FIG. 11 is a diagram showing a spectral characteristic for illustrating a case of estimating spectral image signals of three narrowband lights from image signals of two broadband lights and an image signal of one narrowband light. As shown in FIG. 11, broadband lights are used for B and G, and a narrowband light is used for R. In the spectral estimation section 101c, three spectral estimation image signals e1, e2 and e3 are estimated from the image signals B and G of the two broadband lights and an image signal Rn of one narrowband light.

The three image signals of the two broadband lights B and G and the one narrowband light Rn may be obtained by the color filters of the image pickup device 2A having a spectral characteristic as shown in FIG. 11, or may be obtained by applying return lights of three illumination lights (that is, illumination lights of the two broadband lights B and G and the one narrowband light Rn) generated with the use of a rotating filter as shown in FIG. 2 in the light source device, to a monochrome image pickup device.

Note that, in FIG. 11 also, the three image signals of the two broadband lights and the one narrowband light may be obtained by the color filters of the image pickup device 2A, or a wavelength band of at least one illumination light (Rn) among two or more illumination lights may be caused to be narrower than the wavelength bands of the other illumination lights (B and G) by the light source device radiating two or more illumination lights.

The spectral estimation section 101c estimates the spectral estimation image signals e1, e2 and e3 of the three narrowband lights from the image signals of the two broadband lights B and G and the one narrowband-light image signal Rn by spectral estimation processing. From the image signals of the two broadband lights B and G and the one narrowband-light image signal Rn having wavelength bands as shown in FIG. 11, the spectral estimation image signal e1 of a narrowband light near the wavelength of 600 nm, the spectral estimation image signal e2 of a narrowband light near the wavelength of 630 nm and the spectral estimation image signal e3 of a narrowband light near the wavelength of 540 nm are estimated.

Note that the three spectral estimation image signals e1, e2 and e3 may be obtained from an image signal of one broadband light (for example, an image signal of the broadband light G) and an image signal of one narrowband light Rn by spectral estimation processing.

In FIG. 11, the one narrowband light Rn includes a narrowband light near the wavelength of 600 nm, it may include a narrowband light near the wavelength of 630 nm. Furthermore, the one narrowband light Rn may include neither a narrowband light near the wavelength of 600 nm nor a narrowband light near the wavelength of 630 nm as indicated by dashed-dotted lines in FIG. 11.

Furthermore, the three spectral estimation image signals e1, e2 and e3 may be estimated from an image signal of one broadband light and images signals of two narrowband lights.

Furthermore, the three spectral estimation image signals e1, e2 and e3 may be estimated from image signals of four or more narrowband lights.

In the case of estimating the three spectral estimation image signals from four or more narrowband-light image signals, spectral estimation accuracy is improved in comparison with the case of estimating three image signals of three narrowband lights from three image signals of three narrowband lights. Therefore, the three spectral estimation image signals e1, e21 and e31 may be obtained from four or more narrowband-light image signals, for example, the image signals of the narrowband lights Bn, Gn and Rn by spectral estimation processing.

Figure 12:
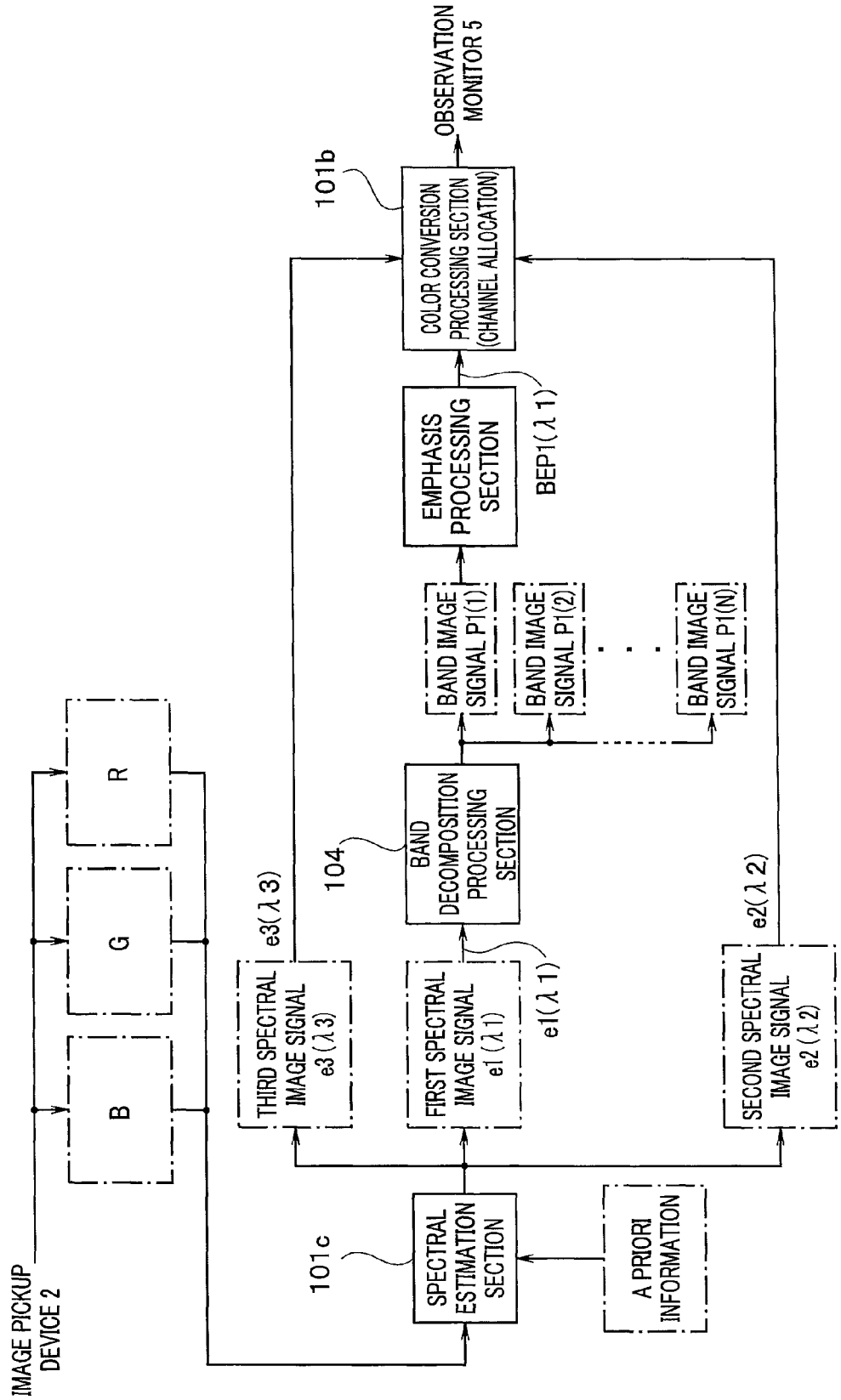
FIG. 12 is a diagram for illustrating a flow of processing for an image obtained from an image pickup device 2 in an image processing section 101A according to the second embodiment.

FIG. 12 is a diagram for illustrating a flow of processing for an image obtained from the image pickup device 2 in an image processing section 101A of the present embodiment.

As shown in FIG. 12, three images, that is, first to third image signals P1, P2 and P3 are inputted to the spectral estimation section 101c from the image pickup device 2. The spectral estimation section 101c estimates and generates three spectral estimation image signals e1, e2 and e3 from the inputted two or three image signals.

Band decomposition processing is performed for one spectral image signal e1 among the three spectral image signals e1, e2 and e3 obtained by the spectral estimation section 101c, in the band decomposition processing section 104. Emphasis processing is performed for a band image signal with a low spatial frequency (a band image signal P1(1) in FIG. 12) obtained by the band decomposition processing, in the emphasis processing section 101a.

That is, the spectral estimation section 101c generates and outputs the spectral estimation image signal e1 as a first image signal by spectral estimation processing on the basis of at least two image pickup signals of return lights from a subject, and the band decomposition processing section 104 performs decomposition processing of the spectral estimation image signal e1.

The color conversion processing section 101b performs color conversion processing by allocation of channels, for the second spectral estimation image signal e2 and the third spectral estimation image signal e3 and the emphasis-corrected image signal BEP1 (λ1) and outputs the signals to the observation monitor 5.

Note that, for example, illuminations of a narrowband light Gn near the wavelength of 540 nm and a narrowband light Rn near the wavelength of 600 nm are radiated as two narrowband lights, and the spectral estimation image signal e2 of a narrowband light near the wavelength of 630 nm is obtained from two obtained image signals Gn and Rn, by spectral estimation. Then, emphasis processing is performed for the spectral estimation image signal e2, and real image signals of the narrowband light Gn near the wavelength of 540 nm and the narrowband light Rn near the wavelength of 600 nm, and the emphasis-processed spectral estimation image signal e2 may be used to display an image.

Furthermore, note that, as for the color filters provided on the surface of the image pickup device, RGB color filters have been described as an example in the present second embodiment, but the color filters may be complementary color filters.

In the endoscope of the present embodiment also, a relatively thick blood vessel existing in a relatively deep part of a living mucosa is emphasized and displayed on the screen of the observation monitor 5 by performing the emphasis processing described above. Therefore, the surgeon can perform desired treatment such as ESD, looking at and confirming the relatively thick blood vessel.

Since the endoscope apparatus 1A described above is capable of displaying a blood vessel existing in a part near the epithelium of a living mucosa using the third spectral estimation image signal e3, it is possible to use an endoscopic image also for diagnosis of living tissue, for example, diagnosis of existence of cancer or range diagnosis for identifying a range of cancer, and for discrimination diagnosis for judging whether an affected part is benignant or malignant, from a state of capillary vessels, for example, degree of concentration or dispersion of the capillary vessels. Furthermore, it is possible to perform invasive depth diagnosis and the like taking into account of a blood vessel in a deeper part.

Note that, in addition to the third spectral estimation image signal e3, fourth and fifth images obtained by further spectral estimation may be used to be color-conversion-processed and displayed on the observation monitor 5.

The wavelength the second spectral estimation signal e2 has shown in FIG. 10 to FIG. 11 may be a light with a longer wavelength band than the minimum value ACmin of the absorption characteristic of hemoglobin in FIG. 5 (here, an absorption coefficient at the wavelength of 730 nm). That is, for the wavelength the second spectral estimation signal e2 has, such a wavelength band that the absorption coefficient is lower than the wavelength the first spectral estimation signal e1 has and the scattering characteristic of living tissue is suppressed, for example, 740 nm, 770 nm, 805 nm, 810 nm, 850 nm, 870 nm, 880 nm, 910 nm, 940 nm, 1020 nm or 1300 nm may be used to obtain advantages equal to those described above (for example, when the wavelength the second spectral estimation signal e2 has is set to any wavelength from 740 nm to 1300 nm, the wavelength the first spectral estimation signal e1 has is set to any wavelength equal to or longer than 576 nm and at least equal to or shorter than 630 nm).

As described above, according to the present embodiment described above, it is possible to provide an endoscope apparatus capable of clearly displaying a blood vessel in a deep mucosa without complicated work of medicine administration being performed.

Third Embodiment

In the first embodiment, at least one narrowband light is actually radiated as an illumination light to living tissue, and the band decomposition processing described above is performed for an image of a return light thereof, and emphasis processing is performed for at least one band image signal obtained by the band decomposition processing. In the second embodiment, the at least one narrowband light is not actually radiated to living tissue. Image information of a return light of each narrowband light is obtained by so-called spectral estimation, and band decomposition processing and emphasis processing as described above are performed for a spectral estimation image signal with each wavelength obtained by the spectral estimation. In the present third embodiment, band decomposition processing is performed for image signals of return lights of actual illumination lights of at least two narrowband lights (or an image signal of a return light of an actual illumination light of one narrowband light and a spectral estimation image signal obtained by spectral estimation). Spectral estimation processing is performed with the use of the at least two band image signals obtained by the band decomposition processing, and emphasis processing is performed for a spectral estimation image signal obtained by the spectral estimation.

Figure 13:
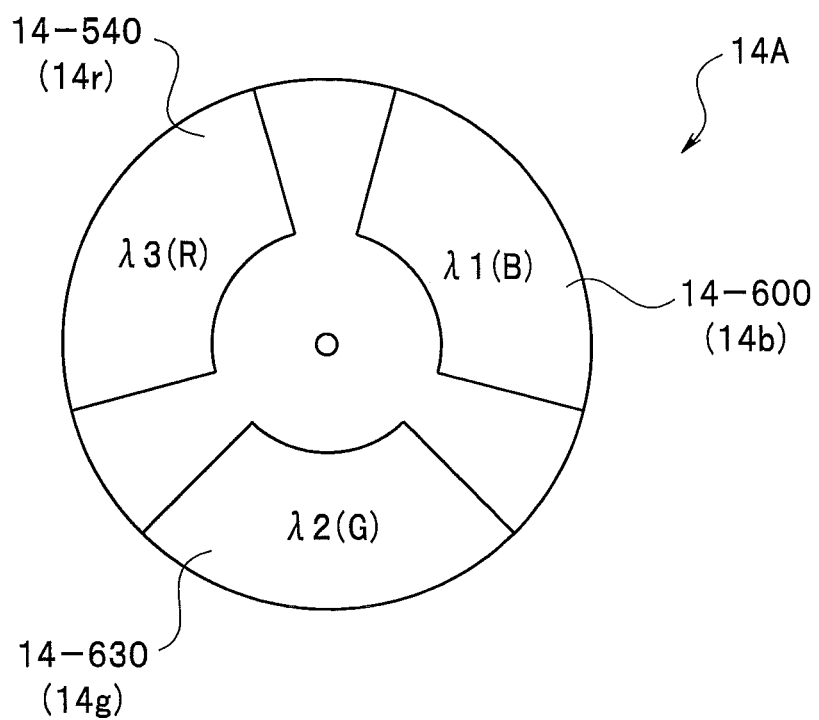
FIG. 13 is a diagram showing a configuration of a rotating filter 14A according to a third embodiment.

A configuration of an endoscope apparatus 1B of the present embodiment is the same as the configuration of the endoscope apparatus 1 shown in FIG. 1, but a configuration of a rotating filter 14A of the present embodiment is different. FIG. 13 is a diagram showing the configuration of the rotating filter 14A of the present embodiment. As shown in FIG. 13, the rotating filter 14A has only the second filter group constituted by the three filters 14-600, 14-630 and 14-540 that transmit lights with three predetermined narrowband wavelengths shown in FIG. 2. Frame-sequential return lights are received by a monochrome image pickup device 2.

Note that, as indicated by parentheses in FIG. 13, the rotating filter 14A may use an RGB filter section constituting a filter set for outputting frame-sequential lights with a spectral characteristic for normal light observation.

Figure 14:
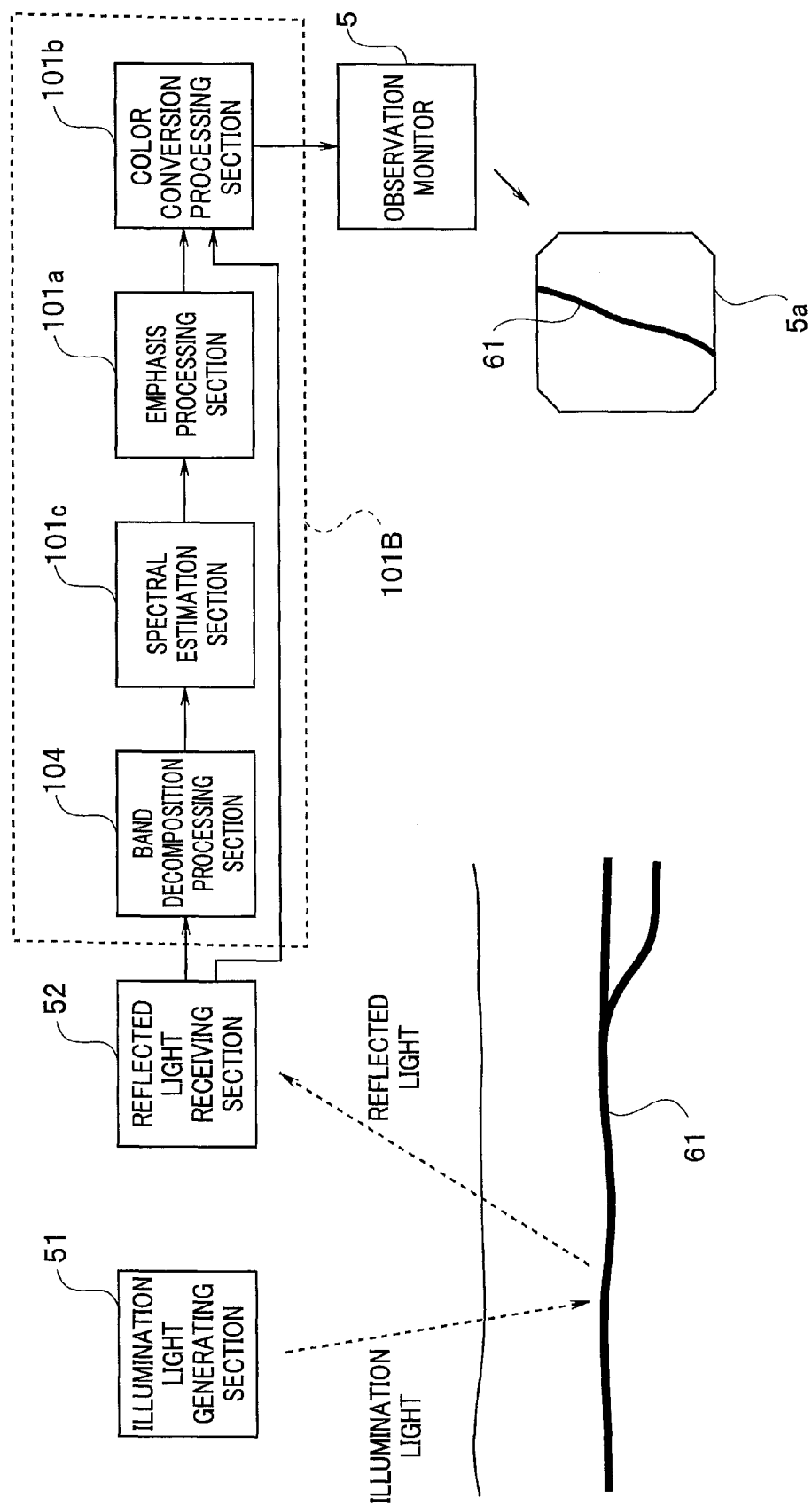
FIG. 14 is a diagram for illustrating a whole process flow in a special light observation mode according to the third embodiment.
Figure 15:
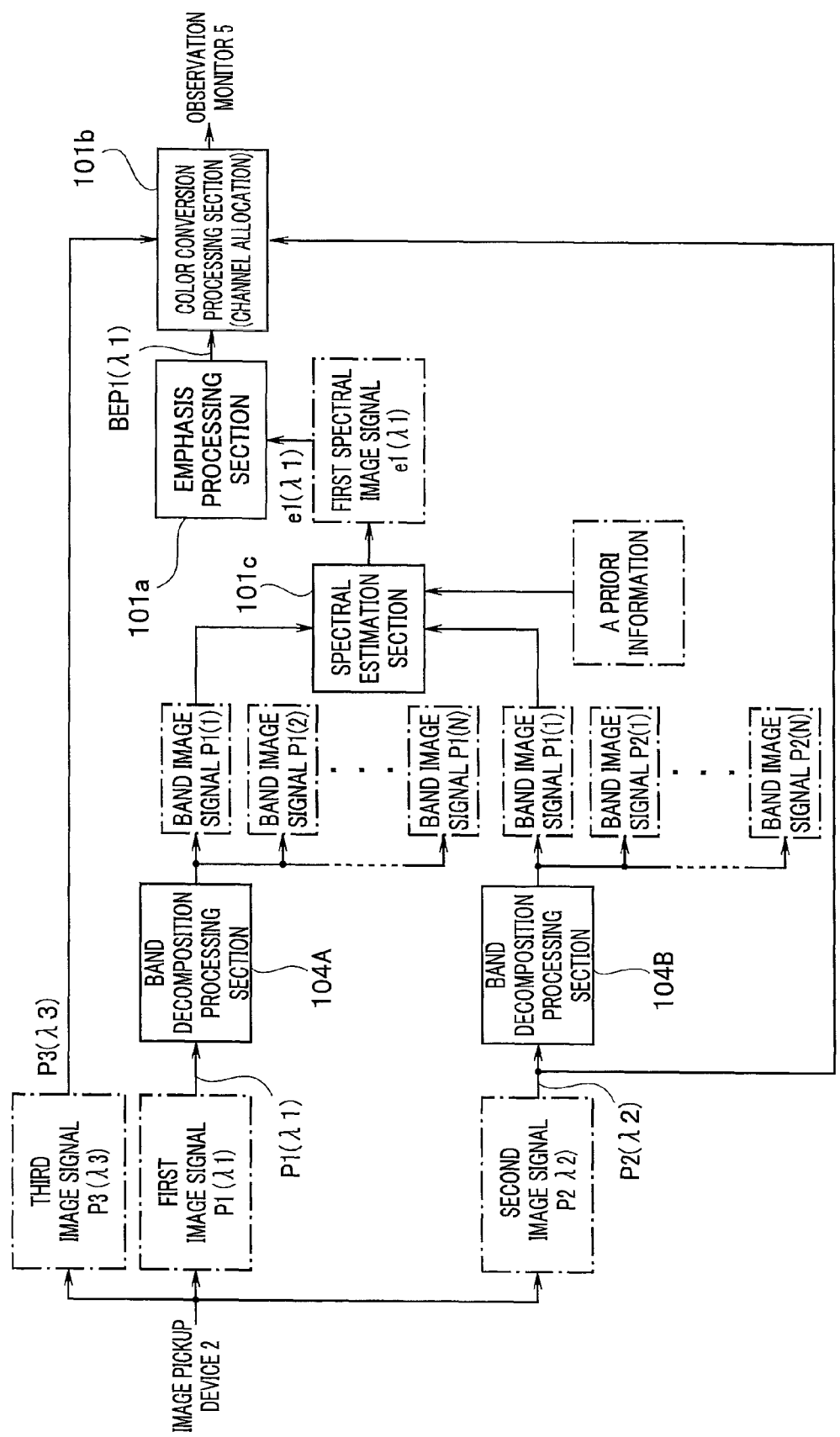
FIG. 15 is a diagram for illustrating a flow of processing for an image obtained from an image pickup device 2 in an image processing section 101B according to the second embodiment.

FIG. 14 is a diagram for illustrating a whole process flow in a special light observation mode according to the present embodiment. In FIG. 14, the same components as those in FIG. 9 are denoted by the same reference numerals and signs and description thereof is omitted. An image processing section 101B includes the band decomposition processing section 104, the emphasis processing section 101a, the color conversion processing section 101b and the spectral estimation section 101c. Since the band decomposition processing section 104 performs band decomposition processing for two image signals, the band decomposition processing section 104 includes two band decomposition processing sections 104A and 104B (FIG. 15). The spectral estimation section 101c is spectral estimation means or a spectral estimation section that generates a spectral estimation image signal by spectral estimation processing on the basis of at least two input signals. Here, at least one spectral estimation image signal e is generated from at least two band image signals obtained by band decomposition processing, and emphasis processing is performed for the spectral estimation image signal e.

Here, more specifically, band decomposition processing by the two band decomposition processing sections is performed for an image signal P1 near the wavelength of 600 nm and a second image signal P2 near the wavelength of 630 nm Then, for each of the image signals P1 and P2, spectral estimation processing is performed with the use of band image signals P1(1) and P2(1) with low spatial frequencies obtained by the band decomposition processing. Emphasis processing is performed for a spectral estimation image signal e1 obtained by the spectral estimation processing, in the emphasis processing section 101a.

FIG. 15 is a diagram for illustrating a flow of processing for an image obtained from the image pickup device 2 in the image processing section 101B according to the present embodiment.

As shown in FIG. 15, three images, that is, the first image signal P1 near the wavelength of 600 nm, the second image signal P2 near the wavelength of 630 nm and a third image signal P3 near the wavelength of 540 nm are inputted from the image pickup device 2 to the image processing section 101B.

The first image signal P1 and the second image signal P2 are band-decomposition-processed by the band decomposition processing section 104A and the band decomposition processing sections 104B, respectively. The band decomposition processing sections 104A and 104B have the same configuration as that of the band decomposition processing section 104 described above. For the first image signal P1, N band image signals P1(1), P1(2), . . . , P1(N) are generated by band decomposition processing, and, for the second image signal P2 also, N band image signals P2(1), P2(2), . . . , P2(N) are generated.

Here, although both of the band decomposition processing sections 104A and 104B generate the same number of band image signals, they may generate a different number of band image signals.

As described above, the spatial frequency fr1 is the lowest, and the spatial frequency is gradually higher from fr2 toward frN. Therefore, among the N band image signals P1(1), P1(2), . . . , P1(N), the band image signal P1(1) is an image signal with the lowest spatial frequency, and, among the N band image signals P2(1), P2(2), . . . , P2(N), the band image signal P2(1) is an image signal with the lowest spatial frequency (for example, band image signals near P1(1) and P2(1) have information about a living structure such as a thicker blood vessel in a deep part. On the other hand, band image signals near P1(N) and P2(N) have information about an uneven surface structure such as a thinner blood vessel or a gland structure in a mucosal epithelium.

The spectral estimation section 101c estimates and generates the spectral estimation image signal e1 of the first image signal P1 near the wavelength of 600 nm on the basis of band image signals with low spatial frequencies (here, the band image signals P1(1) and P2(1) with the lowest spatial frequencies) among multiple band image signals generated by each of the band decomposition processing section 104A and the band decomposition processing sections 104B.

Emphasis processing such as multiplication by a gain coefficient is performed for the spectral estimation image signal e1, in the emphasis processing section 101a, and an emphasis-corrected image signal BEP1 ($\lambda$1) is outputted to the color conversion processing section 101b. The color conversion processing section 101b performs color conversion processing by allocation of channels for the second image signal P2 near the wavelength of 630 nm, the third image signal P3 near the wavelength of 540 nm and the emphasis-corrected image signal BEP1 ($\lambda$1) obtained by emphasis processing, and outputs the signals to the observation monitor 5. The processes in the emphasis processing section 101a and the color conversion processing section 101b are similar to those of the first embodiment.

As described above, the band decomposition processing sections 104A and 104B also perform decomposition processing for decomposition into multiple spatial frequency bands, for the second image signal P2 having the peak wavelength of spectral characteristic between the wavelength band including the maximum value ACmax and the wavelength band at the minimum value ACmin of the absorption characteristic of living tissue, after image pickup by the image pickup device 2. For each of the first and second image signals P1 and P2, the spectral estimation section 101c performs spectral estimation processing, with band image signals with low spatial frequencies among multiple band image signals generated by the band decomposition processing sections 104A and 104B as at least two input signals. Then, the emphasis processing section 101a performs emphasis processing, with a spectral estimation image signal e1 obtained by the spectral estimation processing by the spectral estimation section 101c as a predetermined first band image signal.

Note that, though three narrowband lights are used as illumination lights in the example described above, all or a part of the three may be broadband lights.

Furthermore, note that, though band decomposition processing is performed for the image signal P1 near the wavelength of 600 nm and the second image signal near the wavelength of 630 nm, which are image signals of return lights of actual illumination lights of two narrowband lights in the above example, at least one of the two image signals may be a spectral estimation image signal obtained by generation by spectral estimation.

For example, in order to obtain the multiple band image signals P1(1) to P1(N), the spectral estimation image signal e1 obtained by spectral estimation from the second image signal P2 and the third image signal P3 may be band-decomposition-processed instead of the first image signal P1.

On the contrary, in order to obtain the multiple band image signals P2(1) to P2(N), a spectral estimation image signal e2 obtained by spectral estimation from the first image signal P1 and the third image signal P3 may be band-decomposition-processed instead of the second image signal P2.

As described above, according to the endoscope apparatus of the present embodiment, spectral estimation is performed with the use of two band images with low spatial frequencies among multiple band image signals obtained by band decomposition processing to obtain a spectral estimation image of a relatively thick blood vessel, and emphasis processing is performed for the spectral estimation image.

Note that the three narrowband lights (or broadband lights) in FIG. 15 may be obtained by the color filters of the image pickup device 2A. That is, the three narrowband lights (or broadband lights) may be obtained with the use of the light source device 4A as described in the second embodiment and the color filters of the image pickup device 2A.

Therefore, the same advantages as those of the endoscope apparatuses 1 and 1A described above can be also obtained by the endoscope apparatus 1B of the present embodiment.

Note that, in the present third embodiment, RGB color filters have been described as an example of a case of using color filters provided on the a surface of an image pickup device, the color filters may be complementary color filters.

The wavelength $\lambda$2 the second image signal P2 has, which is shown in FIG. 15, may be a light with a longer wavelength band than the minimum value ACmin of the absorption characteristic of hemoglobin in FIG. 5 (here, an absorption coefficient at the wavelength of 730 nm). That is, for the wavelength the second image signal P2 has, such a wavelength band that the absorption coefficient is lower than the wavelength the first image signal P1 has and the scattering characteristic of living tissue is suppressed, for example, 740 nm, 770 nm, 805 nm, 810 nm, 850 nm, 870 nm, 880 nm, 910 nm, 940 nm, 1020 nm or 1300 nm may be used to obtain advantages equal to those described above (for example, when the wavelength the second image signal P2 has is set to any wavelength from 740 nm to 1300 nm, the wavelength the first image signal P1 has is set to any wavelength equal to or longer than 576 nm and at least equal to or shorter than 630 nm).

In the endoscope of the present embodiment also, a relatively thick blood vessel existing in a relatively deep part of a living mucosa is emphasized and displayed on the screen of the observation monitor 5 by performing the emphasis processing described above. Therefore, the surgeon can perform desired treatment such as ESD, looking at and confirming the relatively thick blood vessel.

Since the endoscope apparatus 1A described above is capable of displaying a blood vessel existing in a part near an epithelium of a living mucosa using the third image signal P3 near the wavelength of 540 nm, an endoscopic image can be used for diagnosis of living tissue, for example, diagnosis of existence of cancer or range diagnosis for identifying a range of cancer, and for discrimination diagnosis for judging whether an affected part is benignant or malignant, from a state of capillary vessels, for example, degree of concentration or dispersion of the capillary vessels. Furthermore, it is possible to perform penetration depths diagnosis and the like taking into account of a blood vessel in a deeper part.

As described above, according to the present embodiment described above, it is possible to provide an endoscope apparatus capable of clearly displaying a blood vessel in a deep mucosa without complicated work of medicine administration being performed.

Common Modification of Respective Embodiments (First Modification)

In the three embodiments and each of modifications thereof described above, the light absorption characteristic of venous blood is given as an example, and two narrowband lights are selected on the basis of the characteristic. However, at least two narrowband lights as described above may be selected on the basis of the light absorption characteristic of arterial blood or the light absorption characteristic of blood of combination of venous blood and arterial blood.

(Second Modification)

In the endoscope apparatus of each embodiment and each modification (including the modification of each embodiment) described above, the light near the wavelength of 600 nm and the light near the wavelength of 630 nm are used as the wavelengths of the first narrowband light NL1 and the second narrowband light NL2, respectively. Preferably, the first narrowband light NL1 and the second narrowband light NL2 are a narrowband light with a wavelength within a wavelength range from 580 to 620 nm having a distribution in a range of a predetermined width and a narrowband light with a wavelength within a wavelength range from 610 to 730 nm having a distribution in a range of a predetermined width, respectively. More preferably, they are a narrowband light with a wavelength within a wavelength range from 585 to 615 nm having a distribution in a range of a predetermined width and a narrowband light with a wavelength within a wavelength range from 620 to 640 nm having a distribution in a range of a predetermined width, respectively.

Therefore, if the first narrowband light NL1 and the second narrowband light NL2 are lights with wavelengths having an absorption characteristic as described above between a maximum value and minimum value of absorption characteristic, the wavelengths of the first narrowband light NL1 and the second narrowband light NL2 are not limited to the light near the wavelength of 600 nm and the light near the wavelength of 630 nm, respectively, and lights with any wavelength are possible. For example, as the wavelengths of the first narrowband light NL1 and the second narrowband light NL2, the light near the wavelength of 610 nm and the light near a wavelength of 645 nm, or the light near the wavelength of 630 nm and the light near a wavelength of 660 nm may be used, respectively.

(Third Modification)

In the endoscope apparatus of each embodiment and each modification (including the modification of each embodiment) described above, the light near the wavelength of 540 nm is used to display capillary vessels in an epithelium of living tissue, as the third narrowband light NL3. However, the wavelength of the third narrowband light NL3 is not limited thereto. For example, as the wavelength of the third narrowband light NL3, the light near the wavelength of 415 nm or 460 nm shorter than the wavelength 540 nm may be used. Especially, in order to obtain information about an epithelium of living tissue, the light near the shorter wavelength of 415 nm or 460 nm is more desirable than the light near the wavelength of 540 nm.

(Fourth Modification)

It has been described that a heat light source lamp, an LED, an LD or the like is used for the light source device of each embodiment and each modification (including the modification of each embodiment) described above. However, other means may be used. For example, a tunable laser may be used as light source means or a light source section. A broadband light generated by exciting a fluorescent body with an LED or an LD may be used.

(Fifth Modification)

In the case of radiating a narrowband light in the endoscope apparatus of each embodiment and each modification (including the modification of each embodiment) described above, it is possible to generate, for example, the narrowband light near the wavelength of 600 nm by a laser, and the narrowband light near the wavelength of 630 nm by an LED. By using a laser beam, it is possible to reduce noise in a depth direction. It is also possible to generate the narrowband light near the wavelength of 600 nm by an LED, and the narrowband light near the wavelength of 630 nm by a laser.

(Sixth Modification)

Though one emphasis processing result is obtained in each embodiment and each modification (including the modification of each embodiment) described above, two or more emphasis processing result may be further obtained.

Figure 16:
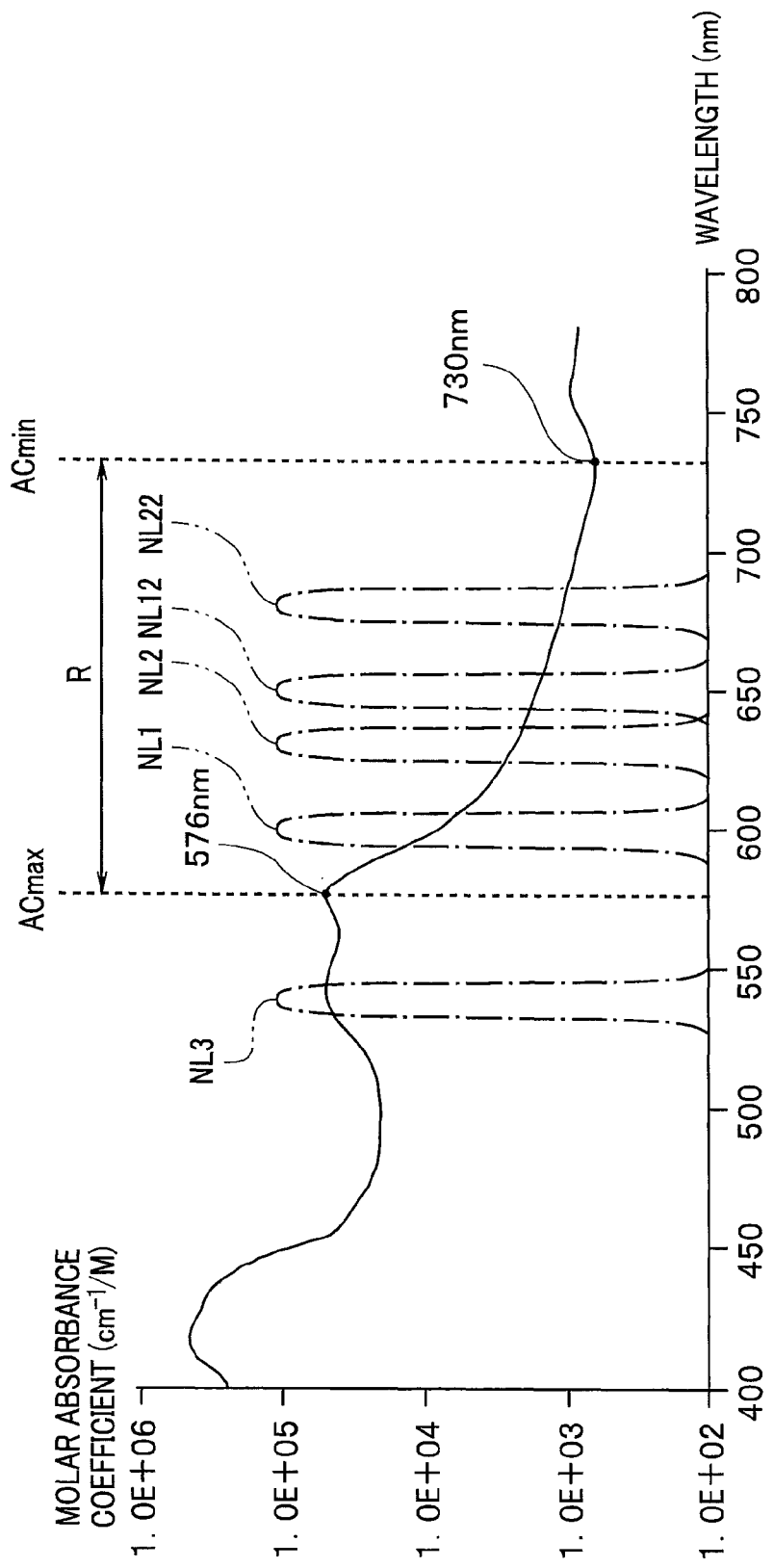
FIG. 16 is a diagram showing the light absorption characteristic of venous blood for illustrating a sixth modification.

FIG. 16 is a diagram showing a light absorption characteristic of venous blood for illustrating the present sixth modification. In FIG. 16, in order that two emphasis processing results can be obtained, emphasis processing is performed for a set of three narrowband lights of a narrowband light NL1 near the wavelength of 600 nm, a narrowband light NL2 near the wavelength of 630 nm and a narrowband light NL3 near the wavelength of 540 nm for one result, and emphasis processing is performed for a set of three narrowband lights of a narrowband light NL12 near the wavelength of 650 nm, a narrowband light NL22 near the wavelength of 680 nm and a narrowband light NL3 near the wavelength of 540 nm for the other. The user can select which combination is to be selected. For example, the user can select by which combination display should be performed, by selecting a mode.

Note that, as another combination, a combination of a narrow band light near the wavelength of 615 nm, a narrow band light near the wavelength of 645 nm and the narrow band light NL3 near the wavelength of 540 nm, a combination of a narrow band light near the wavelength of 630 nm, a narrow band light near the wavelength of 660 nm and the narrow band light NL3 near the wavelength of 540 nm, or the like is also possible.

In the case of the second combination, since the wavelength used is shifted to the long wavelength side in comparison with the first combination, an image of a deeper part is emphasized. Therefore, if the surgeon wants a blood vessel in a deeper part emphasized or blood, bile, urine or the like adheres to a mucosal surface of a living body, a desired blood vessel can be emphasizingly displayed by selecting the second combination.

Emphasis processing for two or more combinations can be performed by increasing the number of combinations of rotating filters in the light source device or increasing the number of spectral estimation image signals estimated by spectral estimation processing.

As combinations of narrowband light wavelengths, it is desirable to have two combinations of a combination of a narrowband light near a wavelength of 580 nm, a narrowband light near the wavelength of 630 nm and a narrowband light near the wavelength of 540 nm, and a combination of a narrowband light near the wavelength of 590 nm, a narrowband light near the wavelength of 630 nm and a narrowband light near the wavelength of 540 nm in the case of emphasizingly displaying a blood vessel at a relatively shallow position from a mucosal surface.

As combinations of narrowband light wavelengths, it is desirable to have two combinations of a combination of a narrowband light near the wavelength of 600 nm, a narrowband light near the wavelength of 630 nm and a narrowband light near the wavelength of 540 nm, and a combination of a narrowband light near the wavelength of 650 nm, a narrowband light near the wavelength of 680 nm and a narrowband light near the wavelength of 540 nm in the case of clearly displaying a blood vessel at a deeper position from a mucosal surface or a blood vessel under a mucosa under blood or the like.

Though two combinations are used in the example described above, three or more combinations are also possible. In the case of three, for example, the three are a first combination of a narrowband light near the wavelength of 600 nm, a narrowband light near the wavelength of 630 nm and a narrowband light near the wavelength of 540 nm, a second combination of a narrowband light near the wavelength of 650 nm, a narrowband light near the wavelength of 680 nm and a narrowband light near the wavelength of 540 nm, and a third combination of a narrowband light near a wavelength of 700 nm, a narrowband light near the wavelength of 730 nm and a narrowband light near the wavelength of 540 nm.

Since multiple emphasis processing results can be obtained as described above, the surgeon can cause a desired blood vessel to be emphasizingly displayed by selecting a combination on a longer wavelength side (for example, a combination of narrowband lights near the wavelength of 650 nm, near the wavelength of 680 nm and near the wavelength of 540 nm) when the concentration of blood or the like adhering to a mucosal surface of a living body is high, and selecting a combination on a shorter wavelength side (for example, a combination of narrowband lights near the wavelength of 590 nm, near the wavelength of 630 nm and near the wavelength of 540 nm) when a blood vessel exists in a relatively shallow part or when the concentration of blood or the like adhering to a mucosal surface of a living body is low.

For example, in the case of the narrowband light near the wavelength of 600 nm and the narrowband light near the wavelength of 630 nm, it is possible to fix the narrowband light near the wavelength of 600 nm and cause the other narrowband light to be variable from near the wavelength of 630 nm to near the wavelength of 730 nm and set arbitrarily. Otherwise, it is also possible to fix the other narrowband light near the wavelength of 730 nm and cause a narrowband light from near the wavelength of 590 nm to near a wavelength of 620 nm to be variably and arbitrarily set. Note that it is also possible to fix the narrowband light near the wavelength of 600 nm and cause the other narrowband light to be arbitrarily set in a wavelength band equal to or more than 730 nm.

By fixing one of wavelength differences of two narrowband lights and causing the other to be variable, it is possible to display a blood vessel in a desired area more clearly.

(Seventh Modification)

In each embodiment and each modification (including the modification of each embodiment) described above, three images are obtained to display a narrowband light image on the observation monitor 5. However, a fourth image may be obtained so that a display image is generated by appropriately selecting images from among four images.

The endoscope apparatus has the narrowband light observation mode in addition to the normal light observation mode, and the surgeon switches the normal light observation mode to the narrowband light observation mode as necessary to perform various treatments. By adding the fourth image, it is possible to easily obtain a display image of each observation mode.

For example, a light source device capable of radiating an illumination light of a blue narrowband light (a broadband light is also possible) with a wavelength shorter than the wavelength of 540 nm is used to obtain the fourth image. The light source device alternately radiates an illumination light of a first combination of a light with the fourth wavelength and a narrowband light near the wavelength of 600 nm, and a second combination of a narrowband light near the wavelength of 540 nm and a narrowband light near the wavelength of 630 nm to a subject. Note that an illumination light of a combination of the light with the fourth wavelength, the narrowband light near the wavelength of 540 nm and the narrowband light near the wavelength of 600 nm, and an illumination light of the narrowband light near the wavelength of 630 nm may be alternately radiated to a subject.

Then, a return light of each illumination light is received by the image pickup device having the RGB color filters. For example, an image of a return light with the fourth wavelength is picked up in the B band of the color filters, and an image of a return light of the narrowband light near the wavelength of 600 nm is picked up in the R band. Note that the color filters of the image pickup device may be complementary ones. Furthermore, note that the image pickup device may be a monochrome image pickup device.

Since images of the respective bands are separated from each other, four monochrome images are obtained in the video processor 7. Note that appropriate color balance adjustment is performed for an image signal of each light to obtain each image.

Then, in the video processor 7, a normal image for the normal light observation mode is generated with the use of images of the four return lights of the light with the fourth wavelength, the narrowband light near the wavelength of 540 nm, the narrowband light near the wavelength of 600 nm and the narrowband light near the wavelength of 630 nm.

In the video processor 7, a first narrowband light image is generated by allocating an image signal of the light with the fourth wavelength to the B and G channels, allocating an image signal of the narrowband light near the wavelength of 540 nm to the R channel, and using two images of the light with the fourth wavelength and the narrowband light near the wavelength of 540 nm.

Furthermore, in the video processor 7, a second narrowband light image is generated with the use of three images of the narrowband light near the wavelength of 540 nm, the narrowband light near the wavelength of 600 nm and the narrowband light near the wavelength of 630 nm.

Note that an image signal of the narrowband light near the wavelength of 600 nm is emphasizingly processed.

Then, in response to an image display instruction by the surgeon, an image generated as described above is selected and displayed on the observation monitor 5.

According to such a configuration, it is possible to display a normal image for the normal light observation and a narrowband light image for the narrowband light observation at the same time or display the normal image and the narrowband light image being overlapped. For example, it is possible to display a normal light image and a first narrowband light image (or a second narrowband light image) in parallel or display the first narrowband light image and the second narrowband light image in parallel.

Furthermore, by allocating an image signal of the light with the fourth wavelength to the B channel, an image signal of the narrowband light near the wavelength of 540 nm to the G channel, and an image signal of the narrowband light near the wavelength of 600 nm to the R channel, or by allocating the image signal of the light with the fourth wavelength to the B channel, the image signal of the narrowband light near the wavelength of 540 nm and the image signal of the narrowband light near the wavelength of 600 nm to the G channel, and the image signal of the narrowband light near the wavelength of 600 nm (or the image signal of the narrowband light near the wavelength of 600 nm and an image signal of the narrowband light near the wavelength of 630 nm) to the R channel, it is possible to generate an overlap image obtained by adding information about a blood vessel in a deep part to a normal image and display the image on the observation monitor 5.

Furthermore, by allocating the image signal of the light with the fourth wavelength to the B channel, the image signal of the light with the fourth wavelength and the image signal of the narrowband light near the wavelength of 600 nm to the G channel, and the image signal of the narrowband light near the wavelength of 600 nm (or the image signal of the narrowband light near the wavelength of 600 nm and the image signal of the narrowband light near the wavelength of 630 nm) to the R channel, it is possible to generate an image in which both of a blood vessel in an epithelium and a blood vessel in a deep part are emphasized and display the image on the observation monitor 5.

Note that the image signal with the fourth wavelength may be generated by spectral estimation.

As described above, according to the present seventh modification, parallel display or overlap display of a normal image and a narrowband light image becomes possible.

As described above, according to each embodiment and each modification (including the modification of each embodiment) described above, it is possible to provide an endoscope apparatus capable of clearly displaying a blood vessel in a deep part of a mucosa without complicated work of medicine administration being performed.

The present invention is not limited to the embodiments described above, and various changes, alterations and the like are possible within a range not changing the spirit of the present invention.

What is claimed is:

1. An endoscope apparatus comprising:
   an illumination section radiating at least one or more illumination lights having a predetermined wavelength band to a subject;
   an image pickup section picking up an image of a return light from the subject based on radiation of the illumination section;
   a band decomposition processing section performing processing for decomposition into multiple spatial frequency bands, for a signal corresponding to a first wavelength band having a narrowband spectral characteristic, in a red band in a visible range between a wavelength band including a maximum value and a wavelength band including a minimum value with regard to a hemoglobin absorption characteristic of living tissue of the subject, after image pickup by the image pickup section;
   an emphasis processing section generating a signal obtained by performing emphasis correction for luminance adjustment for a band image signal with a lowest spatial frequency among multiple band image signals obtained by the decomposition processing by the band decomposition processing section;
   a color conversion processing section performing processing for giving a predetermined coefficient to the signal emphasis-corrected in the emphasis processing section and a signal corresponding to a second wavelength band having an absorption coefficient of the hemoglobin absorption characteristic lower than an absorption coefficient of the hemoglobin absorption characteristic of the signal corresponding to the first wavelength band and having such a spectral characteristic that a scattering characteristic of the living tissue is suppressed, and allocating the signals to respective color channels of BGR; and
   a display section displaying the signals allocated by the color conversion processing section.

2. The endoscope apparatus according to claim 1, wherein the color conversion processing section allocates a signal corresponding to a third wavelength band, the signal being on a shorter wavelength side relative to the red band in the visible range and having the narrowband light spectral characteristic, to the color channel in a state being given the predetermined coefficient in order to obtain epithelium information about the living mucosa.

3. The endoscope apparatus according to claim 2, wherein in a case of allocating the signal corresponding to the third wavelength band to a B channel, the signal corresponding to the first wavelength band to a G channel, and the signal corresponding to the second wavelength band to an R channel, the color conversion processing section gives the predetermined coefficient in a manner that the signal of the B channel is amplified relative to the signal of the R channel.

4. The endoscope apparatus according to claim 1, wherein
   the band decomposition processing section also performs the processing for decomposition into the multiple spatial frequency bands for the signal corresponding to the second wavelength band; and
   the emphasis processing section generates a signal obtained by performing emphasis correction for luminance adjustment for a band image signal with a lowest spatial frequency among multiple band image signals obtained by the decomposition processing of the signal corresponding to the second wavelength band in addition to the signal corresponding to the first wavelength band.

5. The endoscope apparatus according to claim 1, wherein the illumination section radiates a first illumination light having the first wavelength band and a second illumination light having the second wavelength band.

6. The endoscope apparatus according to claim 5, wherein
   the illumination section radiates a third illumination light that can be transmitted by a predetermined distance from an epithelium of the subject; and
   the emphasis processing section generates the emphasis-corrected image signal on the basis of the signal corresponding to the first wavelength band, the signal corresponding to the second wavelength band, the second image signal, and a signal corresponding to a third wavelength band image-picked up by the image pickup section on the basis of radiation of the third illumination light.

7. The endoscope apparatus according to claim 5, wherein
   the endoscope apparatus has a normal light observation mode and a narrowband light observation mode; and
   the illumination section radiates the first illumination light and the second illumination light in the narrowband light observation mode.

8. The endoscope apparatus according to claim 7, wherein
   the illumination section includes a filter for the normal light observation mode and a filter for the narrowband light observation mode for transmitting a light from a light source; and
   the illumination section radiates the first illumination light and the second illumination light in the narrowband light observation mode by emitting the light from the light source through the filter for the narrowband light observation mode.

9. The endoscope apparatus according to claim 1, comprising
   a spectral estimation section generating and outputting a spectral estimation image signal as the signal corresponding to the first wavelength band by spectral estimation processing on the basis of at least two image pickup signals of the return lights from the subject; wherein the band decomposition processing section performs the decomposition processing, with the spectral estimation image signal as the signal corresponding to the first wavelength band.

10. The endoscope apparatus according to claim 1, wherein a peak wavelength of the signal corresponding to the first wavelength band is between wavelengths 585 nm and 615 nm.

11. The endoscope apparatus according to claim 1, wherein a peak wavelength of the signal corresponding to the first wavelength band is a narrowband light near a wavelength of 600 nm.

12. The endoscope apparatus according to claim 1, wherein a peak wavelength of the signal corresponding to the first wavelength band is a narrowband light near the wavelength of 600 nm, and a peak wavelength of the signal corresponding to the second wavelength band is between wavelengths of 610 nm and 730 nm.

13. The endoscope apparatus according to claim 1, wherein a peak wavelength of the signal corresponding to the second wavelength band is a narrowband light near a wavelength of 630 nm.

14. The endoscope apparatus according to claim 1, wherein a peak wavelength of the signal corresponding to the first wavelength band is a narrowband light near the wavelength of 600 nm, and a peak wavelength of the signal corresponding to the second wavelength band is a narrowband light after the wavelength of 730 nm.

15. An endoscope apparatus comprising:
   an illumination section radiating at least one or more illumination lights having a predetermined wavelength band to a subject;
   an image pickup section picking up an image of a return light from the subject based on radiation of the illumination section;
   a band decomposition processing section performing processing for decomposition into multiple spatial frequency bands, for a signal corresponding to a first wavelength band having a narrowband spectral characteristic and a signal corresponding to a second wavelength band having an absorption coefficient of the hemoglobin absorption characteristic lower than an absorption coefficient of the hemoglobin absorption characteristic of the signal corresponding to the first wavelength band and having such a narrowband spectral characteristic that a scattering characteristic of living tissue is suppressed, between a wavelength band including the maximum value and a wavelength band at the minimum value with regard to an absorption characteristic of the living tissue, after image pickup by the image pickup device;
   a spectral estimation section generating a spectral estimation image signal by spectral estimation processing of a band image signal with a low spatial frequency among multiple band image signals generated by the band decomposition processing section for each of the signal corresponding to the first wavelength band and the signal corresponding to the second wavelength band; and
   an emphasis processing section performing emphasis processing for the spectral estimation image signal obtained by the spectral estimation processing of the spectral estimation section.

16. The endoscope apparatus according to claim 15, wherein
   the spectral estimation section performs the spectral estimation processing for a band image signal with a lowest spatial frequency among the multiple band image signals generated by the band decomposition processing section for the signal corresponding to the first wavelength band and the signal corresponding to the second wavelength band.

* * * * *